US011002745B2

United States Patent
Zhang et al.

(10) Patent No.: US 11,002,745 B2
(45) Date of Patent: May 11, 2021

(54) THERAPEUTIC AND DIAGNOSTIC METHODS AND COMPOSITIONS FOR NEURODEGENERATIVE DISEASES

(71) Applicant: Wisconsin Alumni Research Foundation, Madison, WI (US)

(72) Inventors: Su-Chun Zhang, Waunakee, WI (US); Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/012,467

(22) Filed: Jun. 19, 2018

(65) Prior Publication Data

US 2018/0292418 A1  Oct. 11, 2018

Related U.S. Application Data

(62) Division of application No. 14/676,569, filed on Apr. 1, 2015, now Pat. No. 10,024,870.

(60) Provisional application No. 61/974,296, filed on Apr. 2, 2014.

(51) Int. Cl.
*G01N 33/68* (2006.01)
*A61K 38/17* (2006.01)

(52) U.S. Cl.
CPC ..... *G01N 33/6896* (2013.01); *A61K 38/1709* (2013.01); *G01N 2333/47* (2013.01); *G01N 2800/28* (2013.01)

(58) Field of Classification Search
CPC ........... G01N 33/6896; G01N 2800/28; G01N 2333/47; A61K 38/1709
See application file for complete search history.

(56) References Cited

FOREIGN PATENT DOCUMENTS

WO    WO 99/36082    *  7/1999

OTHER PUBLICATIONS

Jordanova et al., Brain, 126:590-597 (Year: 2003).*
Petzold, A., J Neurol Sci, 233:183-198, (Year: 2005).*
Reijn et al., J Neurol., 256:615-619, (Year: 2009).*
Amoroso, M.W., et al. (2013). Accelerated high-yield generation of limb-innervating motor neurons from human stem cells. J. Neurosci. 33, 574-586.
Ban, H., et al. (2011). Efficient generation of transgene-free human induced pluripotent stem cells (iPSCs) by temperature-sensitive Sendai virus vectors. Proc. Natl. Acad. Sci. U. S. A 108, 14234-14239.
Bergemalm, D., et al. (2006). Overloading of stable and exclusion of unstable human superoxide dismutase-1 variants in mitochondria of murine amyotrophic lateral sclerosis models. J. Neurosci. 26, 4147-4154.
Bergeron, C., et al. (1994). Neurofilament light and polyadenylated mRNA levels are decreased in amyotrophic lateral sclerosis motor neurons. J. Neuropathol. Exp. Neurol. 53, 221-230.
Boyd, Justin D., et al. "A high-content screen identifies novel compounds that inhibit stress-induced TDP-43 cellular aggregation and associated cytotoxicity." Journal of biomolecular screening (2013): 1087057113501553.
Bruijn, L.I., et al. (1998). Aggregation and motor neuron toxicity of an ALS-linked SOD1 mutant independent from wild-type SOD1. Science 281, 1851-1854.
Burkhardt, Matthew F., et al. "A cellular model for sporadic ALS using patient-derived induced pluripotent stem cells." Molecular and Cellular Neuroscience 56 (2013): 355-364.
Calvo, A.C., et al. (2012). Genetic biomarkers for ALS disease in transgenic SOD1(G93A) mice. PLoS. One. 7, e32632.
Carpenter, S. (1968). Proximal axonal enlargement in motor neuron disease. Neurology 18, 841-851.
Chambers, S.M., et al. (2009). Highly efficient neural conversion of human ES and iPS cells by dual inhibition of SMAD signaling. Nat. Biotechnol. 27, 275-280.
Chan, Elayne M., et al. "Live cell imaging distinguishes bona fide human iPS cells from partially reprogrammed cells." Nature biotechnology 27.11 (2009): 1033-1037.
Clement, A.M., et al. (2003). Wild-type nonneuronal cells extend survival of SOD1 mutant motor neurons in ALS mice. Science 302, 113-117.
Cote, F., et al. (1993). Progressive neuronopathy in transgenic mice expressing the human neurofilament heavy gene: a mouse model of amyotrophic lateral sclerosis. Cell 73, 35-46.
Dedieu, Jean-Francois, et al. "Long-term gene delivery into the livers of immunocompetent mice with E1/E4-defective adenoviruses." Journal of virology 71.6 (1997): 4626-4637.
Deng, H.X., et al. (1993). Amyotrophic lateral sclerosis and structural defects in Cu,Zn superoxide dismutase. Science 261, 1047-1051.
Egawa, Naohiro, et al. "Drug screening for ALS using patient-specific induced pluripotent stem cells." Science translational medicine 4.145 (2012): 145ra104-145ra104.
Fischer, L.R., et al. (2004). Amyotrophic lateral sclerosis is a distal axonopathy: evidence in mice and man. Exp. Neurol. 185, 232-240.
Furukawa, Y., et al. (2006). Disulfide cross-linked protein represents a significant fraction of ALS-associated Cu, Zn-superoxide dismutase aggregates in spinal cords of model mice. Proc. Natl. Acad. Sci. U. S. A 103, 7148-7153.

(Continued)

*Primary Examiner* — Kimberly Ballard
*Assistant Examiner* — Stacey N MacFarlane
(74) *Attorney, Agent, or Firm* — McDonnell Boehnen Hulbert & Berghoff LLP

(57) ABSTRACT

Methods and compositions relating to motor neurons derived from induced pluripotent stem cells of subjects having a neurodegenerative disease, where the motor neurons exhibit phenotypes characteristic of the neurodegenerative disease, are provided herein. In particular, the present invention provides methods for screening putative therapeutic agents and methods for diagnosing living subjects as having a neurodegenerative disease. In addition, the present invention provides therapeutic gene transfer methods for treating or preventing a neurodegenerative disease in a subject in need thereof.

1 Claim, 26 Drawing Sheets
Specification includes a Sequence Listing.

(56) References Cited

OTHER PUBLICATIONS

Goldstein, M.E., et al. (1983). Microheterogeneity ("neurotypy") of neurofilament proteins. Proc. Natl. Acad. Sci. U. S. A 80, 3101-3105.
Guillaume, D.J., et al. (2006). Human embryonic stem cell-derived neural precursors develop into neurons and integrate into the host brain. J. Neurosci. Res. 84, 1165-1176.
Gurney, M.E., et al. (1994). Motor neuron degeneration in mice that express a human Cu,Zn superoxide dismutase mutation. Science 264, 1772-1775.
Han, S.S., et al. (2011). Constructing and deconstructing stem cell models of neurological disease. Neuron 70, 626-644.
Hirano, A., et al. (1984). Fine structural study of neurofibrillary changes in a family with amyotrophic lateral sclerosis. J. Neuropathol. Exp. Neurol. 43, 471-480.
Hockemeyer, D., et al. (2011). Genetic engineering of human pluripotent cells using TALE nucleases. Nat. Biotechnol. 29, 731-734.
Son, Esther Y., et al. "Conversion of mouse and human fibroblasts into functional spinal motor neurons." Cell stem cell 9.3 (2011): 205-218.
Hu, B.Y., et al. (2010). Neural differentiation of human induced pluripotent stem cells follows developmental principles out with variable potency. Proc. Natl. Acad. Sci. U. S. A 107, 4335-4340.
Ilieva, H., et al. (2009). Non-cell autonomous toxicity in neurodegenerative disorders: ALS and beyond. J. Cell Biol. 187, 761-772.
Israel, M.A., et al. (2012). Probing sporadic and familial Alzheimer's disease using induced pluripotent stem cells. Nature 482, 216-220.
Jiang, H., et al. (2012). Parkin controls dopamine utilization in human midbrain dopaminergic neurons derived from induced pluripotent stem cells. Nat. Commun. 3, 668.
Jonsson, P.A., et al. (2004). Minute quantities of misfolded mutant superoxide dismutase-1 cause amyotrophic lateral sclerosis. Brain 127, 73-88.
Julien, J.P. and Kriz, J. (2006). Transgenic mouse models of amyotrophic lateral sclerosis. Biochim. Biophys. Acta 1762, 1013-1024.
Karch, C.M., et al. (2009). Role of mutant SOD1 disulfide oxidation and aggregation in the pathogenesis of familial ALS. Proc. Natl. Acad. Sci. U. S. A 106, 7774-7779.
Kong, J. and Xu, Z. (1998). Massive mitochondrial degeneration in motor neurons triggers the onset of amyotrophic lateral sclerosis in mice expressing a mutant SOD1. J. Neurosci. 18, 3241-3250.
Krencik, R., et al. (2011). Specification of transplantable astroglial subtypes from human pluripotent stem cells. Nat. Biotechnol. 29, 528-534.
Lee, V.M., et al. (1986). Novel monoclonal antibodies provide evidence for the in situ existence of a nonphosphorylated form of the largest neurofilament subunit. J. Neurosci. 6, 850-858.
Li, X.J., et al. (2008). Directed differentiation of ventral spinal progenitors and motor neurons from human embryonic stem cells by small molecules. Stem Cells 26, 886-893.
Liu, J. et al. (2004). Toxicity of familial ALS-linked SOD1 mutants from selective recruitment to spinal mitochondria. Neuron 43, 5-17.
Marchetto, M.C., et al. (2010). A model for neural development and treatment of Rett syndrome using human induced pluripotent stem cells. Cell 143, 527-539.
Stratford-Perricaudet, L. D., et al. "Widespread long-term gene transfer to mouse skeletal muscles and heart." Journal of Clinical Investigation 90.2 (1992): 626.

Deng, Han-Xiang, et al. "Conversion to the amyotrophic lateral sclerosis phenotype is associated with intermolecular linked insoluble aggregates of SOD1 in mitochondria." Proceedings of the National Academy of Sciences 103.18 (2006): 7142-7147.
Pasinelli, P., et al. (2004). Amyotrophic lateral sclerosis-associated SOD1 mutant proteins bind and aggregate with Bcl-2 in spinal cord mitochondria. Neuron 43, 19-30.
Robberecht, W. and Philips, T. (2013). The changing scene of amyotrophic lateral sclerosis. Nat. Rev. Neurosci. 14, 248-264.
Rosen, D.R., et al. (1993). Mutations in Cu/Zn superoxide dismutase gene are associated with familial amyotrophic lateral sclerosis. Nature 362, 59-62.
Rouleau, G.A., et al. (1996). SOD1 mutation is associated with accumulation of neurofilaments in amyotrophic lateral sclerosis. Ann. Neurol. 39, 128-131.
Schöls, Ludger, et al. "Autosomal dominant cerebellar ataxias: clinical features, genetics, and pathogenesis." The Lancet Neurology 3.5 (2004): 291-304.
Serio, A., et al. (2013). Astrocyte pathology and the absence of non-cell autonomy in an induced pluripotent stem cell model of TDP-43 proteinopathy. Proc. Natl. Acad. Sci. U. S. A 110, 4697-4702.
Sharma, Punita, et al. "High-throughput screening in primary neurons." Methods in enzymology 506 (2012): 331.
Soldner, F., et al. (2011). Generation of isogenic pluripotent stem cells differing exclusively at two early onset Parkinson point mutations. Cell 146, 318-331.
Tu, P.H., et al. (1996). Transgenic mice carrying a human mutant superoxide dismutase transgene develop neuronal cytoskeletal pathology resembling human amyotrophic lateral sclerosis lesions. Proc. Natl. Acad. Sci. U. S. A 93, 3155-3160.
Vierbuchen, Thomas, et al. "Direct conversion of fibroblasts to functional neurons by defined factors." Nature 463.7284 (2010): 1035-1041.
Vijayvergiya, C., et al. (2005). Mutant superoxide dismutase 1 forms aggregates in the brain mitochondrial matrix of amyotrophic lateral sclerosis mice. J. Neurosci. 25, 2463-2470.
Wang, J., et al. (2003). Copper-binding-site-null SOD1 causes ALS in transgenic mice: aggregates of non-native SOD1 delineate a common feature. Hum. Mol. Genet. 12, 2753-2764.
Watanabe, M., et al. (2001). Histological evidence of protein aggregation in mutant SOD1 transgenic mice and in amyotrophic lateral sclerosis neural tissues. Neurobiol. Dis. 8, 933-941.
Wong, P.C., et al. (1995). An adverse property of a familial ALS-linked SOD1 mutation causes motor neuron disease characterized by vacuolar degeneration of mitochondria. Neuron 14, 1105-1116.
Xi, J., et al. (2012). Specification of midbrain dopamine neurons from primate pluripotent stem cells. Stem Cells 30, 1655-1663.
Xu, Z., et al. (1993). Increased expression of neurofilament subunit NF-L produces morphological alterations that resemble the pathology of human motor neuron disease. Cell 73, 23-33.
Yang, Yin M., et al. "A small molecule screen in stem-cell-derived motor neurons identifies a kinase inhibitor as a candidate therapeutic for ALS." Cell Stem Cell 12.6 (2013): 713-726.
U.S. Appl. No. 62/112,441, filed Feb. 5, 2015.
Chen, H. et al. Presentation Abstract of "Dysregulation of neurofilament composition underlies disease-causing SOD1-mediated motor neuron degeneration." Nov. 10, 2013. Waisman Center, Madison, Wisconsin.
Chen, Hong, et al. "Modeling ALS with iPSCs reveals that mutant SOD1 misregulates neurofilament balance in motor neurons" Cell Stem Cell 14.6 (2014): 796-809.

* cited by examiner

FIGS. 1A-1I
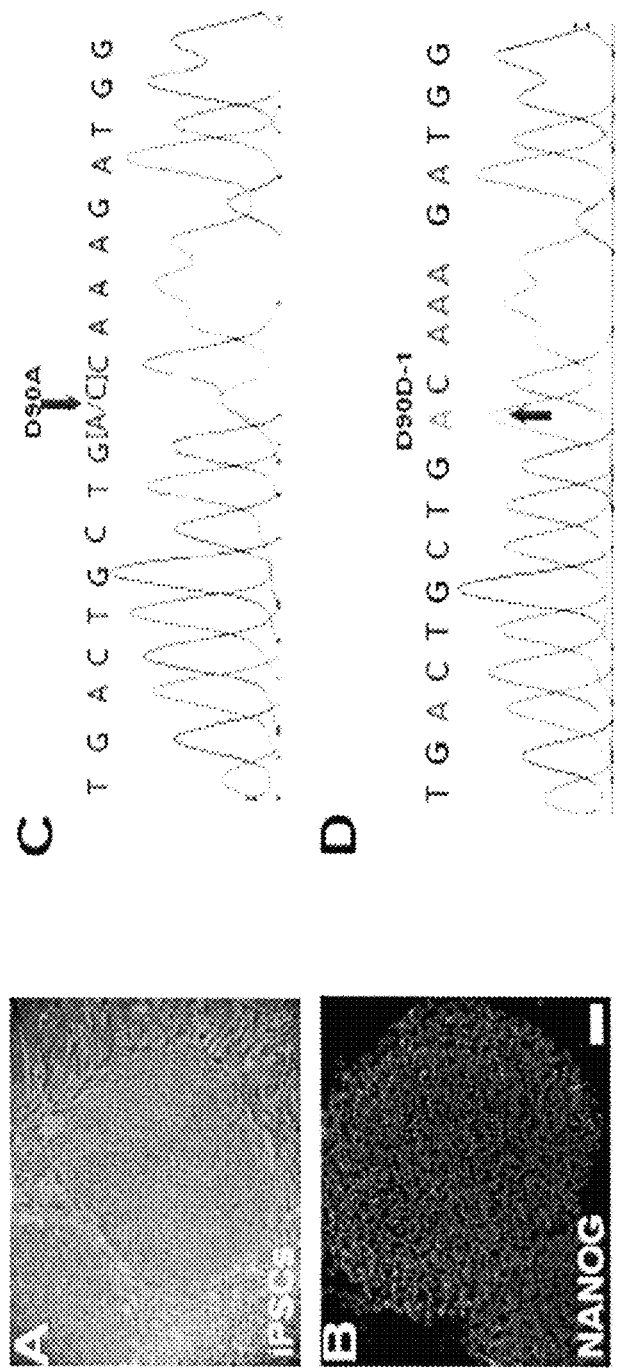
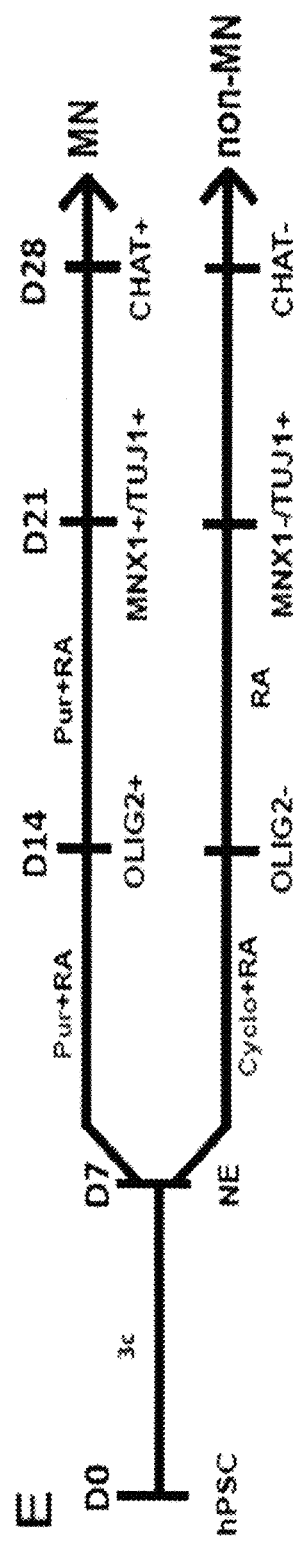

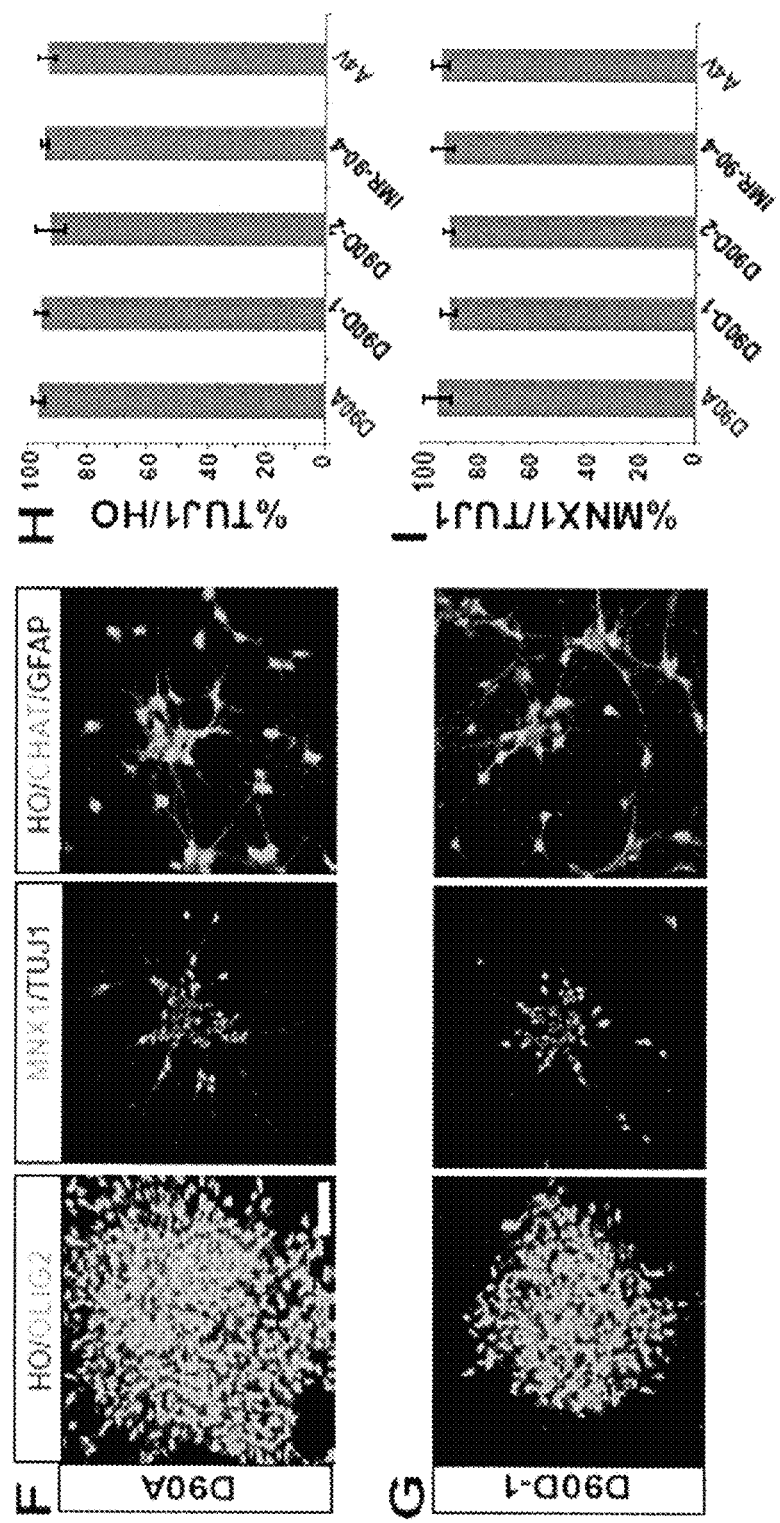
FIGS. 1A-1I, CONTINUED

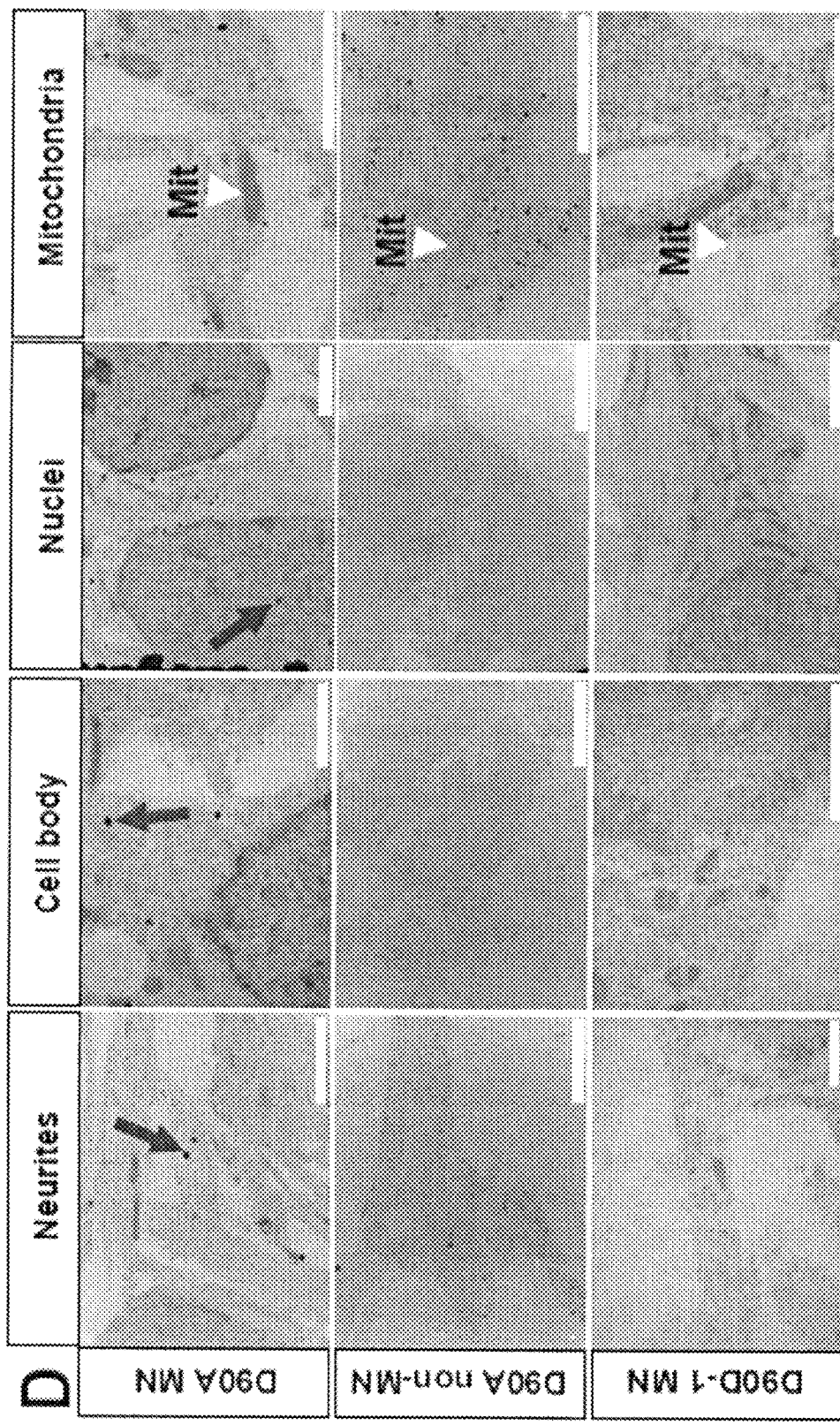
FIGS. 2A-2D, CONTINUED

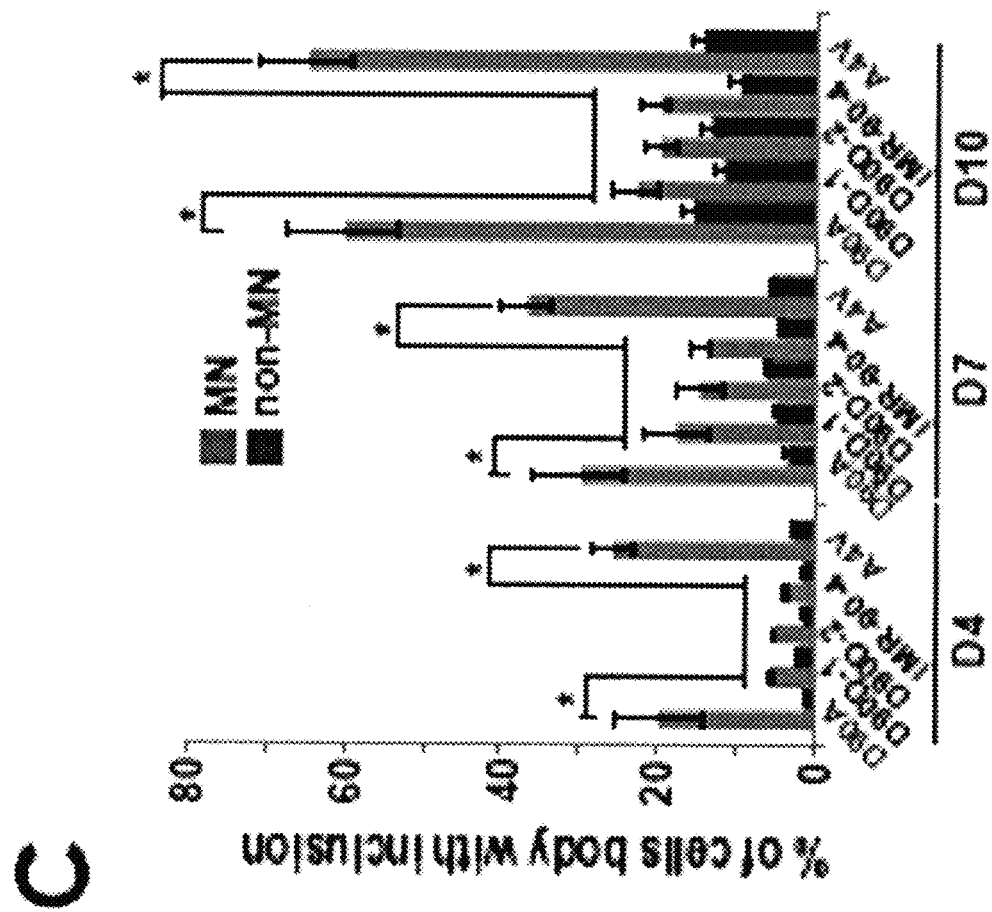
FIGS. 3A-3D, CONTINUED

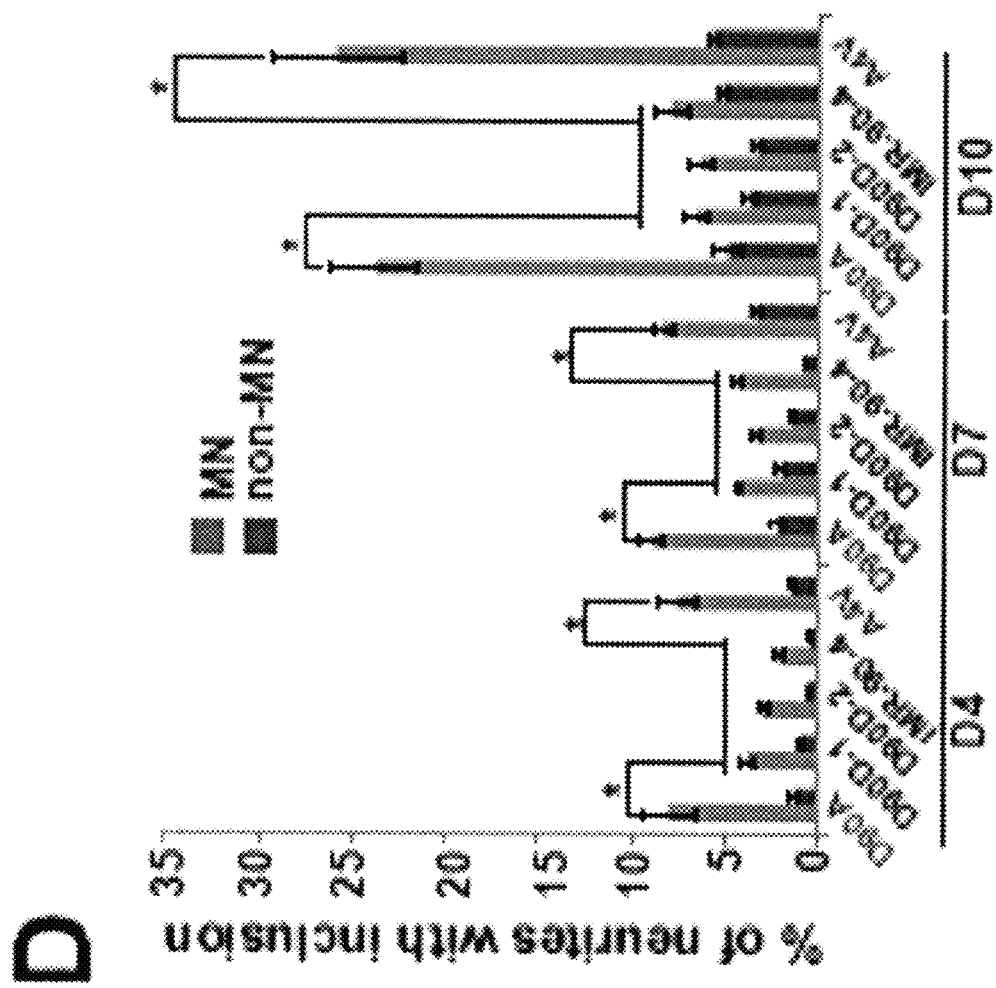
FIGS. 3A-3D, CONTINUED

FIGS. 5A-5G, CONTINUED
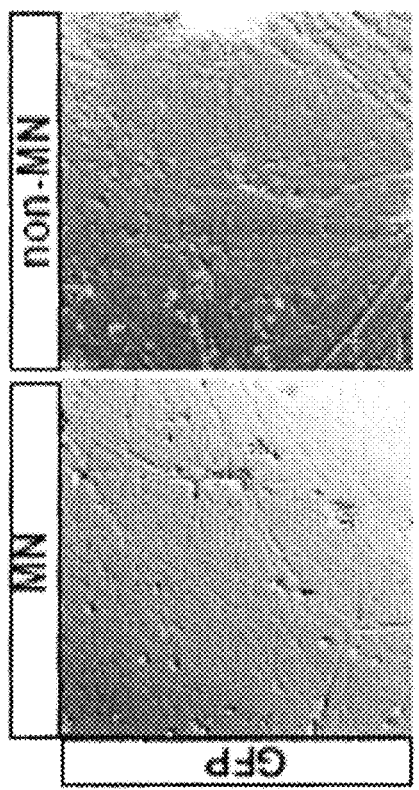
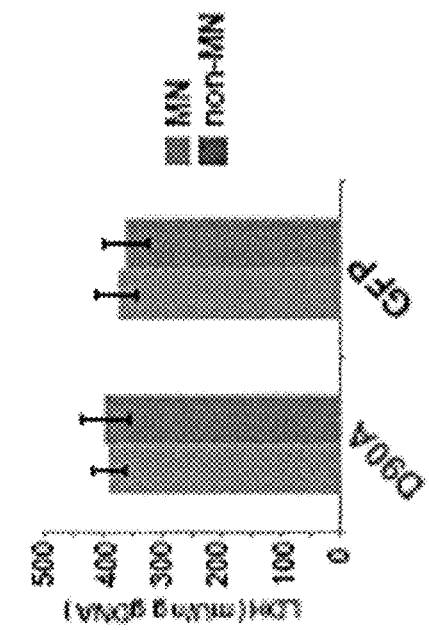
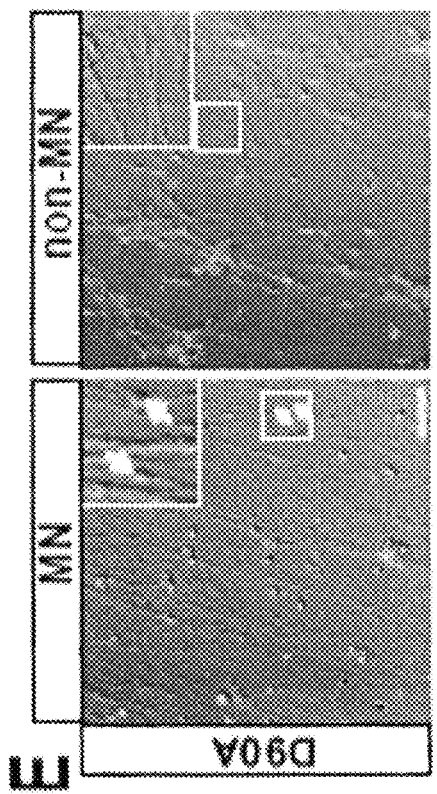
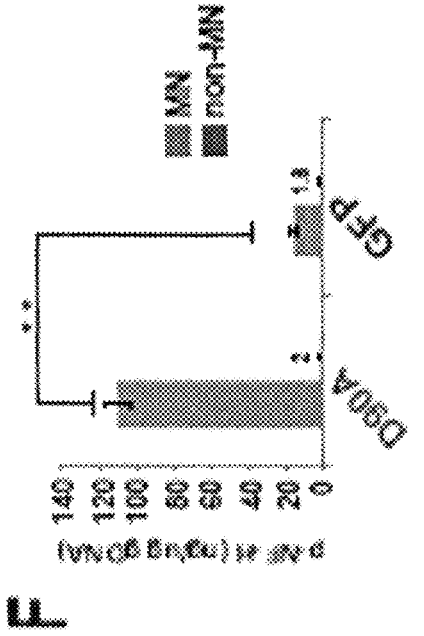

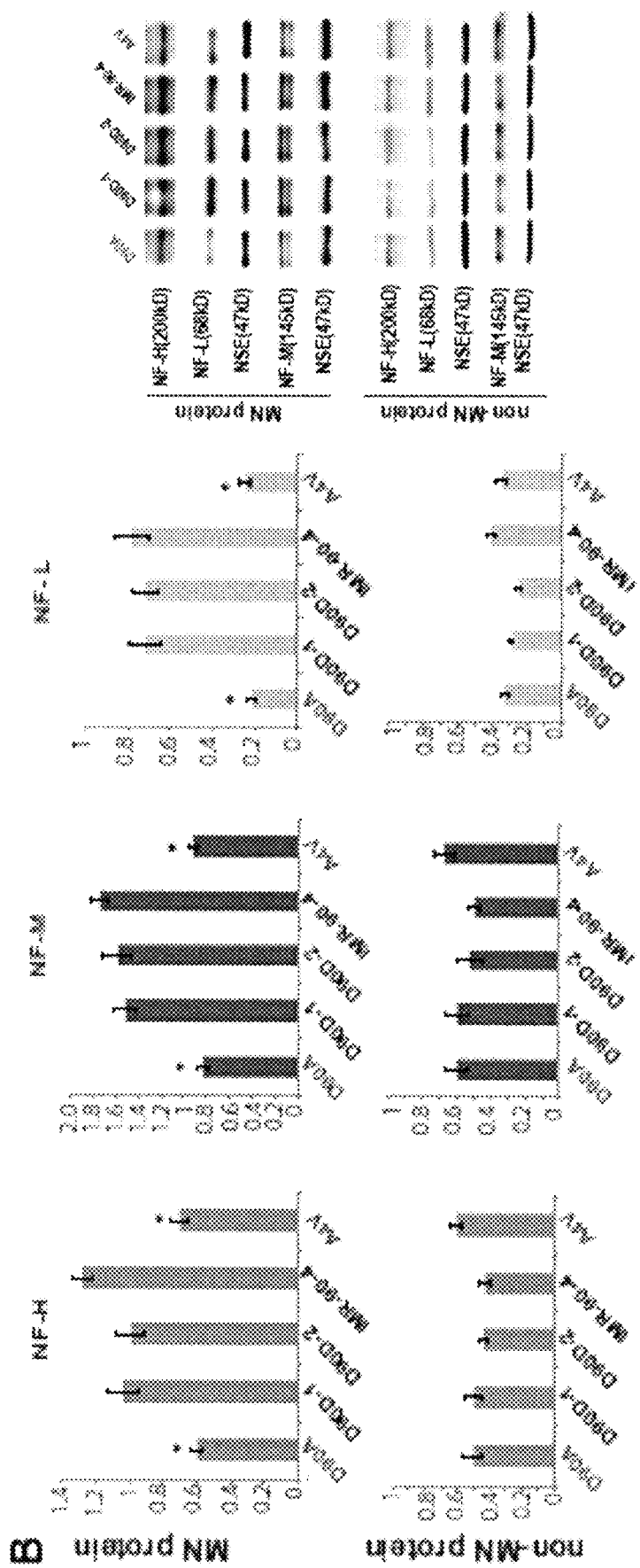
FIGS. 6A-6F, CONTINUED

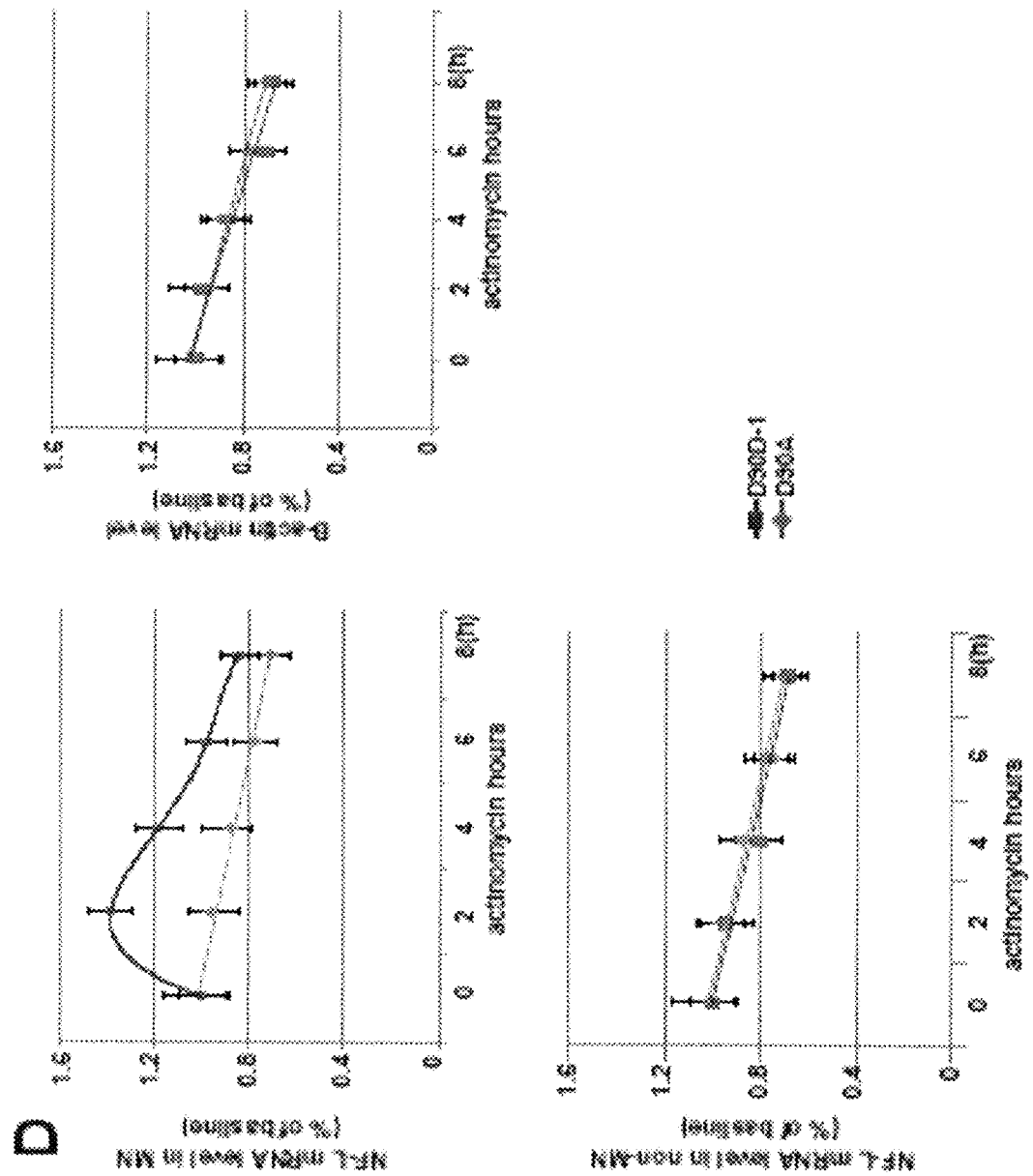
FIGS. 6A-6F, CONTINUED

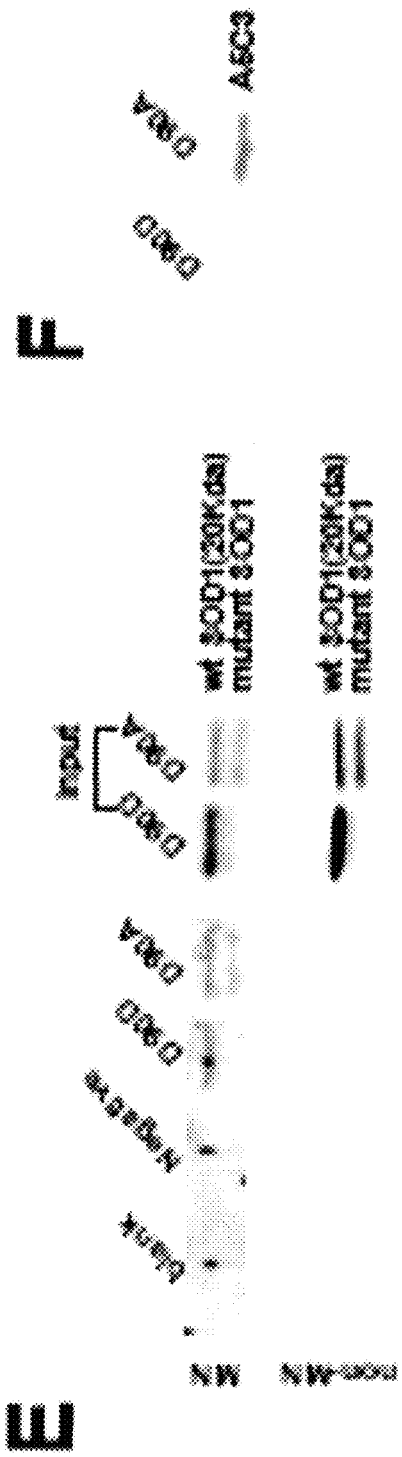
FIGS. 6A-6F, CONTINUED

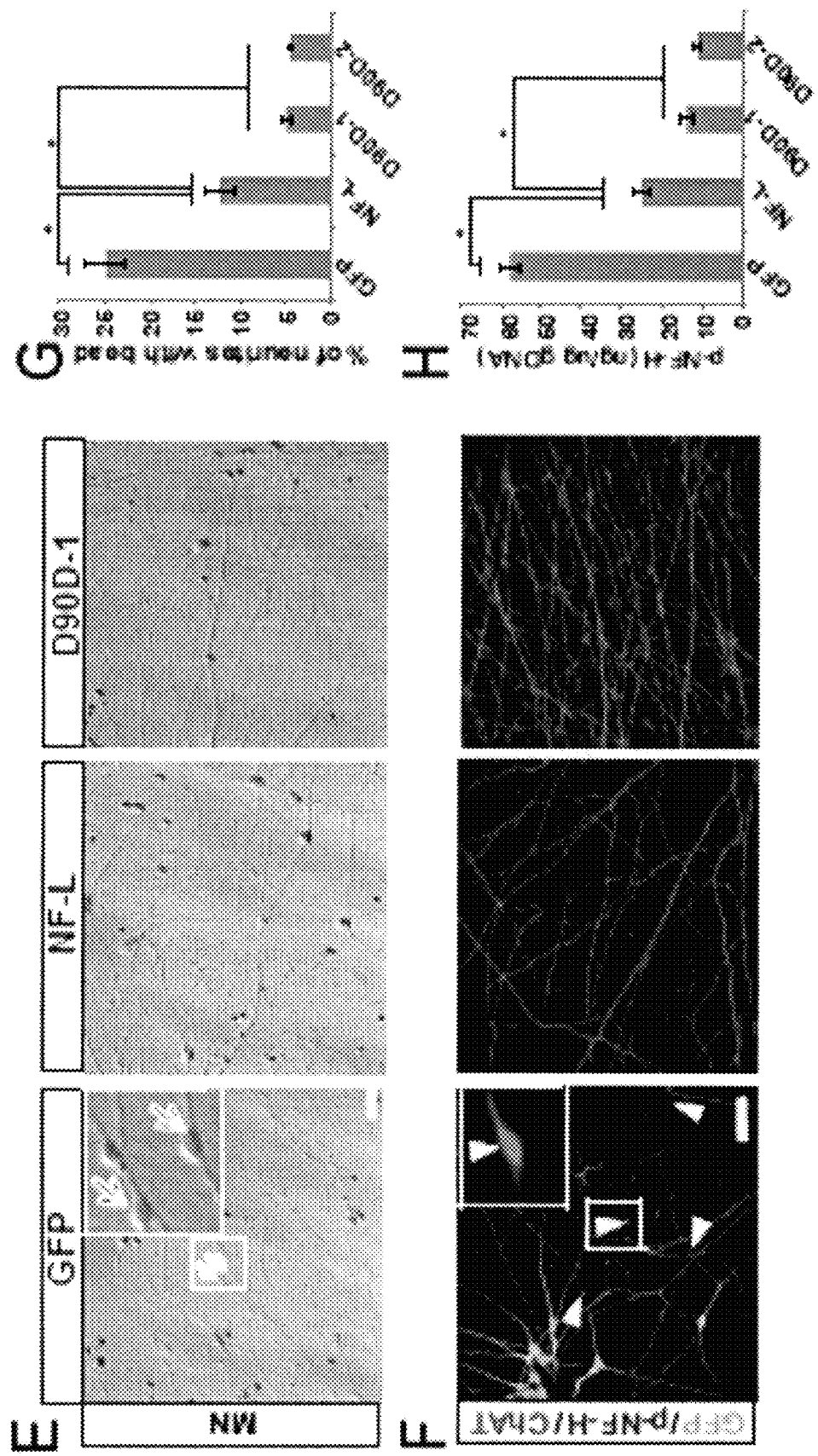
FIGS. 7A-7H, CONTINUED

FIGS. 9A-9B

A.
NF-L nt sequence (SEQ ID NO:1)
```
atgagttccttcagct acgagccgta ctactcgacc tcctacaagc ggcgctacgt ggagacgccc
cgggtgcaca tcttcagcgt gcgcagcggc tacagcaccg cacgctcagc ttactccagc
tactcggcgc cggtgtcttc ctcgctgtcc gtgcgccgca gctactcctc cagctctgga
tcgttgatgc ccagtctgga gaacctcgac ctgagccagg tagccgccat cagcaacgac
ctcaagtcca tccgcacgca ggagaaggcg cagctccagg cagcagaaca ccgcttcgcc
agcttcatcg agcgcgtgca cgagctggag aggtcctgga gccgagctg
ctggtgctgc gccagaagca ctccgagcca tcccgcttcc gggcgctgta cgagcaggag
atccgcgacc tgcgcctggc ggcggaagat gccaccaacg agaagcaggc gctccagggc
gagcgcgaag ggctggagga gacccctgcgc aacctgcagg cgcgctatga agaggagtg
ctgagccgcg aggacgccga gggccggctg atggaagcgc gcaaaggcgc cgacgaggcg
gcgcttcgctc gcgccgagct cgagaagcgc atcgacagct tgatggacga aatctctttt
ctgaagaaag tgcacgaaga ggaatcgcc gaactgcagg cgcagatcca gtacgcgcag
atctccgtgg agatggacgt gaccaagccc gacctttccg ccgcttcaa ggacatccgc
gcgcagtacg agaagctggc cgccaagaac atgcagaacg ctgaggaatg gttcaaggac
cgcttcaccg tgctgaccga gagcgccgcc aagaacaccg acgcgtgcg cgccgccaag
gacgaggtgt ccgagagccg tcgtctgctc aaggccaaga ccctggaaat cgaagcatgc
cgggcatga atgaagcgct ggagaagcag ctgcaggagc tggaggacaa gcagaacgcc
gacattcagc ctatgcagga cacgatcaac aaattagaaa atgaattgag gaccacaaag
agtgaaatgg cacgatacct aaaagaatac caagacctcc tcaacgtgaa gatggctttg
gatattgaga ttgcagctta caggaaactc cagtggctac ttgaaaggcg aggagaccog acctcagtttc
accagcgtgg gaagcataac cagctcctta tcccagagct cccaggtctt tggccgatct
gcctacggcg gtttacagac cagctcctat ctgatgtcca ccgtcctt ccgtcctac
tacaccagcc atgtccaaga ggagcagatc gaagtggagg aaaccattga ggctgccaag
gctgaggaag ccaaggatga gcccccctct gaaggagaag ccgaggagga ggagaaggac
aaggaagagg ccgaggaaga ggaggcagct ggagaggaag aagctgccaa ggagagtct
gaagaagcaa aagaagaaga agaaggaggt gaaggtgaag aaggagagga aaccaaagaa
gctgaagagg aggagaagaa agttgaaggt gctggggagg aacaagcagc taagaagaaa
gattga
```

FIGS. 9A-9B, CONTINUED

B.
NF-L AA sequence: (SEQ ID NO:2)

```
  1 mssfsyepyy stsykrryve tprvhissvr sgystarsay ssysapvsss lsvrrsysss
 61 sgslmpslen ldlsqvaais ndlksirtqe kaqlqdlndr fasfiervhe leqqnkvlea
121 ellvlrqkhs epsrfralye qeirdlrlaa edatnekqal qgeregleet lrnlqaryee
181 evlsredaeg rlmearkgad rlmeaaraele kridslmdei sflkkvheee iaelqaqiqy
241 aqisvemdvt kpdlsaalkd iraqyeklaa knmqnaeewf ksrftvltes aakntdavra
301 akdevsesrr llkaktleie acrgmneale kqlqeledkq nadisamqdt inklenelrt
361 tksemarylk eyqdllnvkm aldieiaayr klleqeetrl sftsvgsits gysqssqvfg
421 rsayqqlqts sylmstrsfp syytshvqee qieveetiea akaeeeakdep psegeaeeee
481 kdkeeaeeee aaeeeeeaake eseeakeeee ggegeegeet keaeeeeekkv egageeqaak
541 kkd
```

FIGS. 10A-10B

A.
NF-H nt sequence: (SEQ ID NO:3)

```
atgatgagc ttcggcggga cgctgggcgc cggacgcgct gctgggcgcc ccgttcgcgc cgtgcatgg cggcggcagc ctccactacg cgctagcccg aaaggtggc
gcaggcggga cgcgctccgc cgcctcaagc cgctggctc tccagcggct gacacggacg tccgtgagct ccgtgtccgc ctcgcccagc cgcttccgtg
gcgcagccgc cgcctcaagc accgactcgc tggacagct aagtgcggg ccggagggct gcatggtggc gcacaaccgc ggtggccacc tcacgcagtg agaaggagca
gctgcagccg ctgaacgacc gcttcgcgcg gtacatcgac aagtgccgc agctggaggc gcacaaccgc cgcgaggtgc gcgaggtgc ggcgctgcgg
cagcagcagg cgggccgctc cgctatgggc gagtgtacg agcgcgaggt ccgcgagatg cgggcgcgg acgaggccg tgctgcgct gggcgcggcg cgcggtcagc
tacgcctgga gcaggagcac ctgctcgagg aggagccga cgtgccgca cgtagacg agaagaggc gcagcgagag gcagcgagg gaggcgagg cgggcgccac
cgcgctgcg cgcttcgcgg aggtgggcga gctgtcccgc ggcggcgcgc gtggacctgc agaagaaggc gcagcgctg cgagagggt gcggtaccct gcagcgcca
caccaggaag aggtgggcga gctgtccgc aattcgcgcg ccagcggtg cgcagccgcg cagatgcagg ccgagacgcg ggagtggttc cgagtgagg tggaccgact
tgacgtcggc gctgcgcgag attcgcgcgc agcttgaag ccacgcggtg cagagcacgc tgcagtccga tgcagtccga cagctgcagg cagctgcagg agagctggag
gtcggaggcg gccaaggtga acacagacgc tatgcgctca gcgcaggagg agataactga gtacccgcgc caggccgaca ccagggaagcg cacagcac
gcactgaaaa gcacagaagg cttcactgga aggcagcgct ctgagctgg ggaccgtcat caggccgaca gaataccagg acctgtcaa tgtcaagatg gctctggaata taggatagc
tggagcgtga gctgaggaaa ccaagtggga agatgccgc ccagctgcga gaatacagg acctgtcaa ctcgcttcca gaagactcc ccaaattcc ctctgtgtcc
cgcttacaga aaactcctgg aagtgaaga gtgtcggat ggctttggcc caattccttt ctcgcttcca actgtgattg tggaggaaca gacagaggag accaagtga
actcacataa aggtgaaag cgaagagaag tcaaagtgg tgagaaagaa aaggggtga aaggaaagag gcagaagggg gagaagaaga
ctgaagaagt gactgaagaa gaggagaaa aggccaaga aggccaagac agtcaccagt aaaaggaaag gcaaagtcac cggctgaggc caagtcccca
aacaaagtct cccccagag aagaggctgc atccccagaa gtcaagtccc ctgagaaagg caaaggaaag gcaaaggaaag accgctgag gccaagtccc
gagaagagg agcaaaaatc cccaagtcca tctcaagctg aggtcaagtc cccagaaag gccaaagga cagcaaagga tcaccggctg aggccaagtc
cagagaggg ggaagcaaaa tctccagctg agtcaagga agaagcaaa aggaagcaa agtccaagtc aggccaagtc agcaaaagta gaggagccaa
tccccggaa gccaagaagg aggccaagtc tccaacgaag gaggaagcaa agtcccctga agtccaagtc aagcaaagtc cccagagaga aagtcccct gagaaggcca
agtccctgag aggccaagtc gaaaccccag gcaaaagtgc ctgagaaagg gtgcaggcaa aagtccctga tcccagtga agccaagtcc cagtgaagga
agaaggcaag tccctgaag aggccaagt gcaaggaaga gcaaagtcc cccagtcccc aaggaaagcag gccaaggcca aagacttga tgtgaagtct aaagacccca
agaaggccag gaaggagaa atctcccctg aaggtgaagaa ctgcagacaa aggccctgca attcccttgaa cagagaagcag gccctgtcca ggagaagctc aagtcccag
gagaaggcca aaggaggcgaa atctcccctg ccaaggcccc tgaaggtgag atccccaaa aaggccctgca cccccgaaa aggagaaaggt gaagaggag gtgaaggagg
aggagcagc cagggaggtg aaagtcaaag agccccaaa agcccagag gaaggcagag cccctgccaa gaaggaacc accaaaaaaca gaggagaaga
aggagcagg gaagaggag gcaccccaaga agggaaagag gtgaggagaa gtgaaggaga agaaggaccc agaaggaacc tgctgtcgaa aagccaaag
aatccaaagt gtaagcccaa aagaaagataa gtaaagagaa ctgaagcaa aaaagaaagtc cccaccccag gatgatgcca tcctgccaag gtggaggtga
aggagcagac taaacccaaa aaggaaagaag aggtagccaa agttagcaag cccaaggga gaggaagcaa agcccaagga accaagcaa ccagcaga aagccaagg
aagatgacaa gcccccagag aaaaaaagaca ccaaggagga gaggaagcaa aagcctgagg agaaccccaa aagcttgagg agaaacccaa aaagccaagg
ctcccagcaa ggccacagaa gacaagggccg gtaa
```

FIGS. 10A-10B. CONTINUED

B.
NF-H AA sequence: (SEQ ID NO:4)
```
  1 mmsifggadal lgapfaplhg ggslhyalar kggaggtrsa agsssgfhsw trtsvssvsa
 61 spsrfrgaga asstdsldtl sngpegcmva vatsrsekeq lqalndrfag yidkvrqlea
121 hnrslegeaa alrqqgagrs amgelyerev remrgavlrl gaargqlrle qehllediah
181 vrqrlddear qreeaeaaar alarfageae aarvdiqkka qalgeecgyl rrhhqeevge
241 llgqiggsga agaqmqaetr dalkcdvtsa lreiraqleg havqstlqse ewfrvrldrl
301 seaakvntda mrsaqeeite yrrqlgartt elealkstkd slerqrsele drhgadiasy
361 qeaiqqldae lrntkwemaa qlreyqdlln vkmaldieia ayrkllegee crigfgpipf
421 slpeglpkip svsthikvks eekikvveks eketviveeq teetqvteev teeeekeake
481 eegkeeegge eeeaeggeee tksppaeeaa spekeakspv keeakspaea kspekeeaks
541 paevkspeka kspakeeaks kspaeeaks ppeakspeke eakspaevks pekakspake eakspaeaks
601 pekakspvke eakspaeaks pvkeeakspa evkspekaks pekakspe ptkeeakspe kakspekeea
661 kspekakspv kaeakspeka kspvkaeaks kspvkeeaks pekakspvke eakspekaks pvkeeakspe
721 kakspvkeea ktpekakspv keeakspeka kspekaktld vkspeaktpa keeearspadk
781 fpekakspvk eevkspekak splkedakap ekeipkkeev kspvkeeeekp qevkvkeppk
841 kaeeekapat pkteekkdsk keeapkkeap kpkveekkep avekpkeskv eakkeeaedk
901 kkvptpekea pakvevkeda kpkektevak kepddakake pskpaekkea apekkdtkee
961 kakkpeekpk teakakeddk tlskepskpk aekaekssst dqkdskppek atedkaakgk
```

FIGS. 11A-11B

A.
NF-M nt sequence (SEQ ID NO:5)
atgagct acacgttgga ctcgctgggc
aaccgtccg cctaccggcg ggtaaccgag accgctcga gcttcagccg cgtcagcggc tcccgtcca gtggcttccg ctcgcagtcg tggtcccgcg gctcgcccag
caccgtgtcc tcctcctata agcgcagcat gctccgcccg cgcctcgctt acagctcggc catgctcagc tccgcgaga gcagccttga cttcagccag tccttgtccc
tgcttcaacgg cggctccgga cccggcggcg actacaagct gtcccgctcc aacgagaagg agcagctgca ggggctgaac gaccgctttg ccggctacat agagaaggtg
cactacctgg agcagcagaa taaggagatt gaggcggaga cgcaggcgca caggcctcgc acgccagct gggcgacgcg tacgaccagg agatccggca
gctcgcgcc accctggaga tggtgaacca cagtgcagc cgagacatcc ccacctggag gaagacatcc acccggctcaa ggagcgcttt ggaggagagg
cgggttgcg cgacgacact gaggcggcca tccgcgcgt gggcaaagac atcgaggagg cgtcgtgt caaggtggag ctgacaaga aggtgcagtc gctgcaggat
gaggtggcct tcctgcggag caaccacgag gaggagtgg ccgacccttct ggcccagatc caggcatcgc acatcacggt ggacgcaaa gactacctga agacagacat
ctcgacgcg ctgaaggaaa tccgctccca gctcgaaage cactcagacc agaatatgca ccaggccgaa gagtggttca aatgccgcta cgccaagctc accgaggcgg
ccgagcagaa caaggagagg ctccgctccg atcgccgag ccaaggaaga gatcgccgag ctggcccgcc agctgcagtc cgagcagatc cggcagcatc cggtgcgcgg caccaaggag
tccctggagc ggcagctcag cgacatcgag gagcgccaca cacacgacct ccagcagct ggaaaatgag cttcggggca caaagtgga
aatggctcgt catttgcgcg aataccagga cctcctcaac gtcaagatgg ctcggatat agaaatcgct gcgtacagaa aactcctgga gggtgaagag actagatta
gcacaaaattgc aggaagcatc actggccac tgtatacaca ccgaccacc catacaatat ccagtaagat tcagaaaacc aagtgggaag ctcccaagct taaggtccaa
cacaaattttg tcgaggagat cataagagaa aggatgagaa gtcagaaatg gaagaggccc tgacagccat tacaagaaga ttggccgttt ccatgaagaa
agagaagaaa gaagcagcag aagaagaaa agggaaagcc agaagaagga ggaagaaccc gaatgctgaa agctgcccaa aagctctcca aaggagaagt tgcaccttgaa gttaaaagaag
aggaaaagg aaggtgagca aggaagaaga gaaacagaga ctgaagctga aggagaggga gatgaggaga gaacagccaa gagaggggat ccgagaagga aggtctctcct aggaagttggc
taccaaggag gagctggtgg cagatgccaa cggtggaaaag ccaagtctcc tgtgccaaaa ccagtggaag tcaccagtgg agagaaagg caagtctcct gtgcccagtt
caccagtgga agagaaaagc aagtctcctg tgcccaagtc gcccaaatca gtcctcctgt gccaaaatca ccagtggaag aggagaagca ccagtggaag aggagaagaa
tcaaatcac cagtggaaga agagtaagag aaaaggaaga gcaaagtggagaag gcaaagcaag agaaccaaga ggatgtgcca aagctgagtc ccctgtaaag gaggaagctg
aaaggaagtc aaggaagctc ggtcaccatc accaaatcgg taaagtgca ctggagaga gagaccaaaa aagatgcag caggagaaag agaaggaaaa gagggagga
tggcagagt ggtcaccatc gtgaggagga aggggaagctc accagaagct agggatccag gaaggagac atagctgca aagggggaa atgaggaggt agaaggaaa gaggaggtag agcggaggac
gagggagga gtgaggagga gggaagtgg aaagggtcca agggtagaag gaagggaagg gagaaggctgca gaaggggaga aaaaaga gagaggtag aaaaaagga gagaaggta taaaaagtgag gagaaaagtgg
tggtgaccaa ggcagtggga gggaagagga gggaagcgt gtcaccaatg gcctagactt gagccagca gatggtgct accaaataca tcactaaatc tgtaaccgtc acttcaaaag ttgaagagca tgaagagacc
tttgaggaga aacgtagtgc aactagtgtc tactaaaag gtagaaaaag gtagaaaaag tcacttcaca cgccatagta aaggaagtca cccagagtga ctaa

NF-M AA sequence: (SEQ ID NO:6)

```
  1 msytldslgn psayrrvtet rssfsrvsgs pssgfrsqsw srgspstvss sykrsmlapr
 61 layssamlss aessldfsqs sslinggsqp gqdyklsrsn ekeqlgglnd rfagyiekvh
121 yleggnkeie aeiqalrqkq ashaqlgday dqeirelrat lemvnhekaq vqldsdhlee
181 dihrlkerfe eearlrddte airalrkdi eeaslvkvel dkkvqslqde vaflrsnhee
241 evadllaqiq ashitverkd ylktdistal keirsqlesh sdqnmhqaee wfkcryaklt
301 eaaeqnkeai rsakeelaey rrqlqsksle lesvrgtkes lerqlsdlee rhnhdissyg
361 dtlgqlenel rgtkwemarh lreyqdilnv kmaldielaa yrkllegeet rfstfagslt
421 gplythrppi tlsskigkpk veapklkvqh kfveelieet kvedekseme ealtalteel
481 avsmkeekke aaeekeeepe aeeeevaakk spvkatapev keeegekeee egqeeeeed
541 egaksdqaee ggsekegsse keegeqeege pveekgkspv pkspveekgk spvpkspvee kqkspvpksp
601 lvadakvekp ekakspvpks pveekgkspv pkspveea kskaevgkge qkeeeekevk eapkeekvek
661 veekgkspvs kspveekaks pvpkspveea eavaevvtit ksvkvhleke tkeegkplgg ekekekagge
721 keekpkdvpe kkkaespvke eavaevvtit ksvkvhleke tkeegkplgg ekekekagge
781 ggseeeegsdk gakgsrkedi avngevegke evegetkekg sgreeekgvv tngldlspad
841 ekkggdksee kvvvtktvek itseggdgat kyitksvtvt qkveeheetf eeklvstkkv
901 ekvtshaivk evtgsd
```

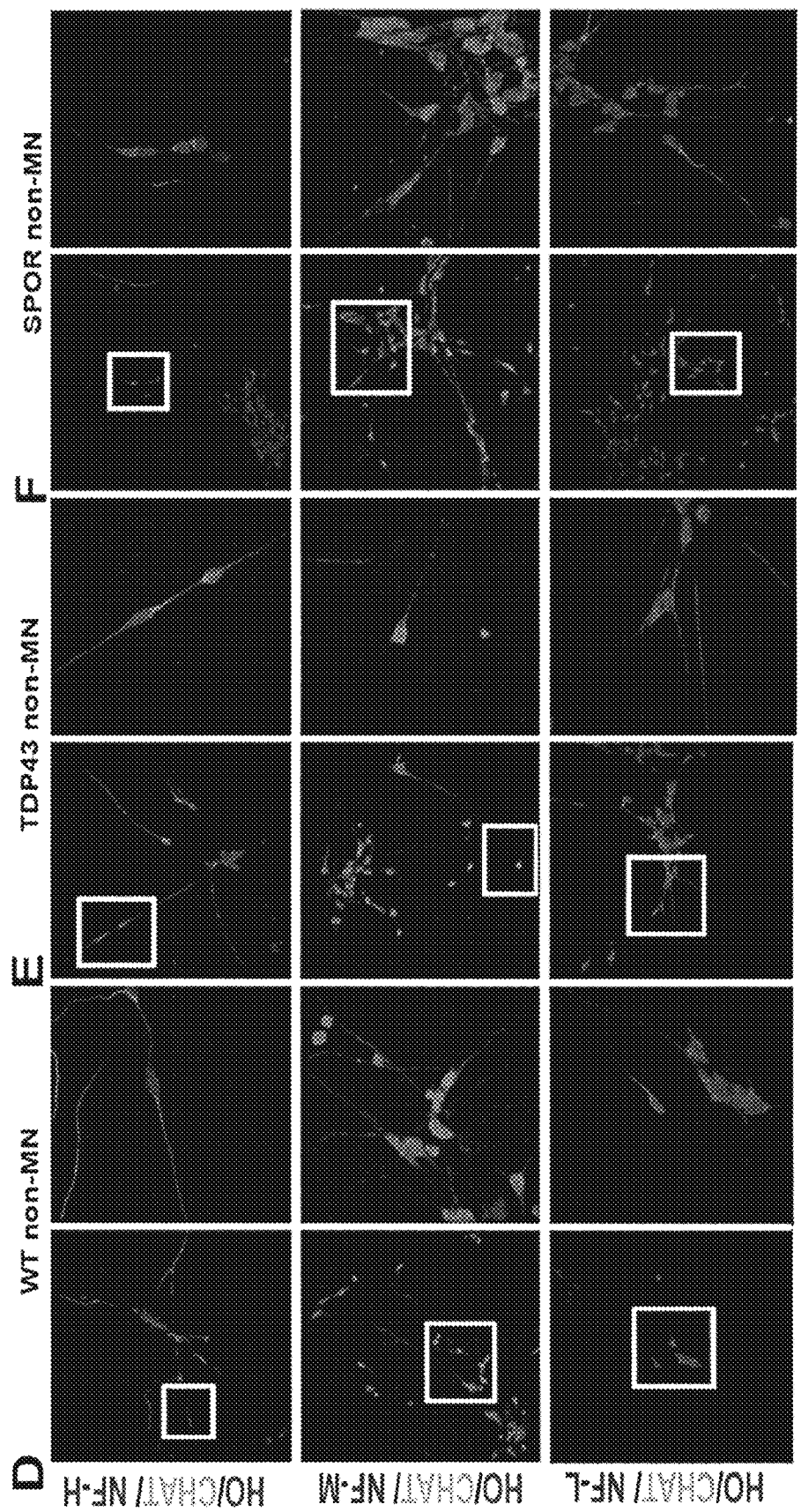

THERAPEUTIC AND DIAGNOSTIC METHODS AND COMPOSITIONS FOR NEURODEGENERATIVE DISEASES

CROSS-REFERENCE TO RELATED APPLICATIONS

This application is a divisional application of U.S. patent application Ser. No. 14/676,569, filed Apr. 1, 2015, which claims the benefit of U.S. Provisional Patent Application No. 61/974,296, filed Apr. 2, 2014, each of which is incorporated herein by reference as if set forth in its entirety.

STATEMENT REGARDING FEDERALLY SPONSORED RESEARCH OR DEVELOPMENT

Not applicable.

BACKGROUND OF THE INVENTION

Neurodegenerative disease is a term that encompasses a range of pathologies that primarily affect neurons of the central nervous system. Neurodegenerative diseases are typically characterized by the progressive degeneration and/or death of neurons in different regions of the nervous system and the resulting impairments in movement and mental functioning. Neurodegenerative diseases, which are incurable and often debilitating, have an enormous impact on the lives of affected individuals and their families as well as society as a whole.

Parkinson's disease, amyotrophic lateral sclerosis (ALS), and Alzheimer's disease are the most well-known neurodegenerative diseases, but other conditions, such as Spinal Muscle Atrophy, Charcot-Marie-Tooth disease, Huntington's disease, spinocerebellar ataxias, Guillain-Barré syndrome, Parkinson's disease-related disorders, and other motor neuron diseases belong to the same clinical group. Pathologies common to genetically inherited and sporadic cases of these neurodegenerative diseases are the accumulation of misfolded proteins, especially neurofilament (NF), and axonal degeneration. It remains unknown how protein aggregation, mitochondrial dysfunction, glutamate toxicity, and disrupted calcium homeostasis promote axonal degeneration or why these processes selectively affect specific populations of neurons, such as motor neurons in ALS, although some evidence suggests that protein aggregates disrupt axonal transportation and consequently promote retraction of motor neuron axonal degeneration before the loss of cell bodies.

Accordingly, there remains a need for a better understanding of the etiopathology of neurodegenerative diseases. In addition, there remains a need in the art for methods for detecting neurodegenerative conditions before clinical symptoms manifest, for facilitating accurate diagnosis of neurodegenerative disease, for monitoring disease progression, and for identifying candidate therapeutic agents to slow, halt, or reverse neurodegeneration.

SUMMARY OF THE INVENTION

In one aspect, the present invention provides a method of diagnosing neurodegenerative disease in a subject. The method can comprise the steps of obtaining induced pluripotent stem (iPS) cells from somatic cells of a subject, where the iPS cells are capable of differentiation into neurons; culturing the iPS cells under conditions suitable to differentiate the iPS cells into neurons; and detecting an indicator of neurofilament aggregation or neurite degeneration in the iPS cell-derived neurons, where increased neurofilament aggregation or neurite degeneration relative to neurons derived from iPS cells of an individual not having neurodegenerative disease indicates that the subject has a neurodegenerative disease, and thereby diagnosing neurodegenerative disease in the subject.

In some cases, the neurodegenerative disease can be selected from the group consisting of amyotrophic lateral sclerosis (ALS), Alzheimer's Disease (AD), Parkinson's Disease (PD), a PD-related disorder, Huntington's Disease (HD), Charcot-Marie-Tooth disease (CMT), Spinocerebellar ataxia (SCA), Spinal Muscle Atrophy (SMA), and Guillain-Barré syndrome (GBS). The neurodegenerative disease can be ALS, SMA, or CMT, and the subject's iPS cells can differentiate into motor neurons. Detecting neurofilament aggregation can comprise determining a level of NF-L mRNA in the subject's iPS cell-derived motor neurons. In some cases, the method can further comprise detecting a level of phosphorylated neurofilament in a biological sample of the subject. The biological sample of the subject can be cerebrospinal fluid. The neurodegenerative disease can be Alzheimer's disease, and the subject's iPS cells can differentiate into glutamatergic neurons or cholinergic neurons. The neurodegenerative disease can be Parkinson's disease or a PD-related disorder, and the subject's iPS cells can differentiate into dopaminergic neurons. The neurodegenerative disease can be spinocerebellar ataxia and the subject's iPS cells can differentiate into granular neurons.

In another aspect, the present invention provides a method of detecting a neurodegenerative disease in a subject. The method can comprise the steps of determining a level of NF-L mRNA in neurons derived from iPS cells obtained from somatic cells of a subject; relating the determined level to a reference level of NF-L; and thereby detecting neurodegenerative disease in the subject based on a reduced level of NF-L relative to the reference level. The neurodegenerative disease can be selected from the group consisting of amyotrophic lateral sclerosis (ALS), Alzheimer's Disease (AD), Parkinson's Disease (PD), a PD-related disorder, Huntington's Disease (HD), Charcot-Marie-Tooth disease (CMT), Spinocerebellar ataxia (SCA), Spinal Muscle Atrophy (SMA), and Guillain-Barré syndrome (GBS). In some cases, the neurodegenerative disease is ALS, where the neurons can be motor neurons, and where the reference level can be a level of NF-L mRNA in motor neurons derived from iPS cells of an individual having ALS. The reduced level of NF-L mRNA can be at least 50% lower than the reference.

In a further aspect, the present invention provides a method for treating a neurodegenerative disease in a subject in need thereof. The method can comprise administering one or more recombinant nucleic acid sequences encoding at least a portion of NF-L to the subject, where the nucleic acid sequences can be targeted to neurons, and where expression of NF-L in targeted neurons can treat the neurodegenerative disease. The neurodegenerative disease can be selected from the group consisting of amyotrophic lateral sclerosis (ALS), Alzheimer's Disease (AD), Parkinson's Disease (PD), a PD-related disorder, Huntington's Disease (HD), Charcot-Marie-Tooth disease (CMT), Spinocerebellar ataxia (SCA), Spinal Muscle Atrophy (SMA), and Guillain-Barré syndrome (GBS). The nucleic acid sequences can be administered in a vector. The vector can be a virus or virus-derived. The virus can be selected from the group consisting of an adenovirus, retrovirus, herpes virus, and adeno-associated virus. The vector can be a replication defective adenovirus.

In another aspect, the present invention provides a method for protecting against neurite degeneration in a subject in need thereof. The method can comprise administering one or more nucleic acid sequences encoding NF-L to tissue of the subject, where the nucleic acid sequences are targeted to neurons of the tissue, and where expression of NF-L protects the targeted neurons from neurite degeneration. The subject can have been diagnosed or can be suspected of having a neurodegenerative disease. The neurodegenerative disease can be selected from the group consisting of amyotrophic lateral sclerosis (ALS), Alzheimer's Disease (AD), Parkinson's Disease (PD), a PD-related disorder, Huntington's Disease (HD), Charcot-Marie-Tooth disease (CMT), Spinocerebellar ataxia (SCA), Spinal Muscle Atrophy (SMA), and Guillain-Barré syndrome (GBS). The nucleic acid sequences can be administered in a vector. The vector is a virus or virus-derived. The virus can be selected from the group consisting of an adenovirus, retrovirus, herpes virus, and adeno-associated virus.

In a further aspect, the present invention provides a method of evaluating a candidate neuroprotective agent. The method can comprise the steps of contacting a candidate neuroprotective agent to neurons derived from induced pluripotent stem (iPS) cells obtained from somatic cells of a human subject having a neurodegenerative disease, where the neurons exhibit a phenotype typical of the neurodegenerative disease; and evaluating the contacted neurons for a neuroprotective effect of the agent relative to non-contacted iPS cell-derived neurons of the subject. The neurodegenerative disease can be selected from the group consisting of amyotrophic lateral sclerosis (ALS), Alzheimer's Disease (AD), Parkinson's Disease (PD), a PD-related disorder, Huntington's Disease (HD), Charcot-Marie-Tooth disease (CMT), Spinocerebellar ataxia (SCA), Spinal Muscle Atrophy (SMA), and Guillain-Barré syndrome (GBS). The neuroprotective effect can be selected from the group consisting of a reduction in severity of neurodegeneration, a delay in onset of neurodegeneration, a reduction in severity of neurofilament (NF) aggregation, and increased motor neuron viability in vitro.

In another aspect, the present invention provides a recombinant nucleic acid molecule comprising a motor neuron-specific promoter operably linked to a nucleic acid sequence encoding a human NF-L polypeptide. The invention also provides a vector comprising said nucleic acid molecule. The vector can be a plasmid. The vector can be a virus or virus-derived. The virus can be selected from the group consisting of an adenovirus, retrovirus, herpes virus, and adeno-associated virus. The vector can be a replication defective adenovirus.

In a further aspect, the present invention provides a kit for diagnosing a subject predisposed to or suspected of developing a neurodegenerative disease or suffering from a neurodegenerative disease. The kit can comprise at least one oligonucleotide primer capable of hybridizing to a at least a portion of a NF-L target nucleic acid; at least one reference corresponding to a level of NF-L target nucleic acid; at least one buffer or reagent; and a container. The at least one oligonucleotide primer can comprise the nucleotide sequence of any of SEQ ID NO:7-8. The neurodegenerative disease can be selected from the group consisting of ALS, SMA, and CMT.

BRIEF DESCRIPTION OF THE DRAWINGS

FIGS. 1A-1I demonstrate iPS cell generation, neural differentiation, and mutation correction. (FIG. 1A) Contrast image of iPS cell colonies generated by Sendai virus. (FIG. 1B) Immunofluorescent image of NANOG expression in D90A SOD1 iPS cells. (FIGS. 1C-D) DNA sequencing showing heterozygous nucleotides (A/C) in D90A (C) and homozygous nucleotide A in corrected (D90D) (D) SOD1 iPS cells. (FIG. 1E) Schematic protocol for MN and non-MN differentiation. 3c: 3 small molecular compounds (SB431542, LDN193189, and CHIR99021); Pur: purmorphamine; Cyclo: cyclopamine. (FIGS. 1F-G) ALS (D90A) and genetically corrected ALS (D90D) iPS cells differentiated to OLIG2$^+$ MN progenitors at day-14, MNX1$^+$ post-mitotic MNs at day-21, and CHAT$^+$ maturing MNs at day-28. (FIGS. 1H-I) Quantification of TUJ$^+$ neuronal population among total Hoechst labeled (HO) cells (FIG. 1H) and MNX1$^+$ MNs among neurons (FIG. 1I). Scale bar=50 µm.

(FIG. 2A) Allelic imbalance assay showing the ratio of mutant (A) and wt (C) copy of SOD1 transcripts in fibroblasts (FIB), reprogrammed stem cells (iPS), and their differentiated neuroepithelia (NEP), MN progenitors (MNP), MNs, and non-MNs. (FIG. 2B) RT-qPCR analysis showing SOD1 mRNA expression in MNs and non-MNs. (FIG. 2C) Representative Western blots and relative SOD1 expression levels (to GAPDH) in MNs and non-MNs. (FIG. 2D) SOD1 immuno-EM in neurites, cytoplasm, nuclei, and mitochondria of MN and non-MN cultures. Arrows=clusters of gold particles. No contrast staining for ALS non-MNs to permit better views of fine gold particles. Scale bar=2 µm.

(FIG. 3A) Immunofluorescent images of NF-H, NF-M, and NF-L in CHAT$^+$ MNs. NF staining in the insets is magnified on the right panel. Arrows indicate NF aggregates in the cell body; arrowheads indicate NF aggregates in neurites. Scale bar=50 µm. (FIG. 3B) EM showing NF arrangement in cell body (left) and neurites (right) of MN cultures. Scale bar=2 µm. (FIGS. 3C-D) Quantification of NF aggregate-containing cell bodies (FIG. 3C) and neurites (FIG. 3D) in MNs and non-MNs at day-4, 7, and 10 after plating. *p<0.05.

(FIG. 4A) Colorimetric measurement of LDH (normalized to gDNA) in culture media from MN and non-MN cultures. (FIG. 4B) Cleaved caspase3 staining (arrows) and (FIG. 4C) quantification. (FIG. 4D) Phase contrast images of MNs and non-MNs at day-10. Arrows indicate bead-like swellings in neurites. Inset is magnified in upper-right. (FIG. 4E) Immunofluorescent images of p-NF-H in MNs and non-MNs. Arrowheads indicate bead-like structures in neurites. Inset magnified in upper right. (FIG. 4F) Quantification of beads on neurites. (FIG. 4G) ELISA quantification of p-NF-H in media (normalized to gDNA). *p<0.01. Scale bar=50 µm.

(FIG. 5A) Western blots and relative expression of SOD1 (to GPDH) in MNs and non-MNs derived from hESCs expressing D90A SOD1 or EGFP. (FIG. 5B) Immunofluorescent images of NF-H, NF-M, and NF-L in CHAT$^+$ cells from SOD1- and EGFP-expressing hESCs. NF staining in the insets is magnified on the right panel. Arrows indicate NF aggregates in the cell body; arrowheads indicate NF aggregates in neurites. (FIGS. 5C, D) Quantification of NF aggregate-containing cell bodies (FIG. 5C) and neurites (FIG. 5D) at day-4, 7, and 10 after plating neurons. (FIG. 5E) Phase contrast images of MNs and non-MNs from mutant SOD1-and EGFP-expressing hESCs. Arrows indicate bead-like formations in neurites. Inset is magnified in upper-right. (FIGS. 5F, G) p-NF-H (FIG. 5F) and LDH (FIG. 5G) in culture media from MN and non-MN cultures derived from SOD1- or EGFP-expressing hESCs. *p<0.05; **p<0.01. Scale bar=50 μm.

(FIG. 6A) Relative levels of mRNAs for NF-L, NF-H, and NF-M, and β-actin mRNA in ALS (D90A) and corrected (D90D) MNs in the presence of actinomycin D measured by RT-qPCR (p<0.05 between D90A and D90D). (FIG. 6B) Relative expression and representative Western blots of NF-H, NF-M, and NF-L in MNs and non-MNs as compared to neuron-specific enolase (NSE). (FIG. 6C) The proportion of NF-L among total NF protein in MNs (upper panel) and non-MNs (lower panel). *p<0.05 between ALS (D90A, A4V) and genetically corrected ALS (D90D) or wt (IMR-90-4) cells. (FIG. 6D) Relative levels of NF-L and β-actin mRNA in ALS (D90A) and corrected (D90D) MNs in the presence of actinomycin D measured by RT-qPCR (p<0.05 between D90A and D90D). (FIG. 6E) Western blotting for mutant SOD1 in MN and non-MN samples pulled down by the 3'UTR NF-L mRNA probe. (FIG. 6F) Input samples were blotted for A5C3 antibody.

(FIG. 7A) Western blots and relative (to neuron-specific enolase (NSE)) expression of NF-H, NF-M, and NF-L in MNs from GFP-, NF-L-expressing ALS (D90A) iPS cells as well as genetically corrected (D90D1 & 2) ALS iPS cells. (FIG. 7B) The proportion of NF-L among total NF protein in the presence of 1 μg/ml of DOX. (C, D) Quantification of NF aggregate-containing cell bodies (FIG. 7C) and neurites (FIG. 7D) in MNs. (FIG. 7E) Phase contrast images of MNs at day-10. Arrows indicate bead-like swellings in neurites. Inset is magnified in upper-right. (FIG. 7F) Immunofluorescent images of pNF-H in MNs. Arrowheads indicate bead-like structures in neurites. (FIG. 7G) Quantification of bead-like formations. (FIG. 7H) ELISA quantification of pNF-H in media from MN cultures. Scale bar=50 μm. *p<0.05.

(FIG. 8A) Immunofluorescent staining for NF-L in sporadic and control (IMR90) MNs at day-10. Inset is magnified on the right. Arrow indicates aggregate in cell body and arrowhead indicates inclusion in neurite. (FIG. 8B) Electron micrograph shows NF aggregate in a MN neurite from ALS but not control (IMR-90). (FIG. 8C) Quantification of NF-L mRNA by RT-qPCR between control (IMR-90) and sporadic ALS MNs.

FIGS. 9A-9B present (FIG. 9A) nucleotide (SEQ ID NO:1) and (FIG. 9B) amino acid (SEQ ID NO:2) sequences for NF-L.

FIGS. 10A-10B present (FIG. 10A) nucleotide (SEQ ID NO:3) and (FIG. 10B) amino acid (SEQ ID NO:4) sequence for NF-H.

FIGS. 11A-11B present (FIG. 11A) nucleotide (SEQ ID NO:5) and (FIG. 11B) amino acid (SEQ ID NO:6) sequences for NF-M.

DETAILED DESCRIPTION OF THE INVENTION

Figures 2A, 2B, 2C, 2D:
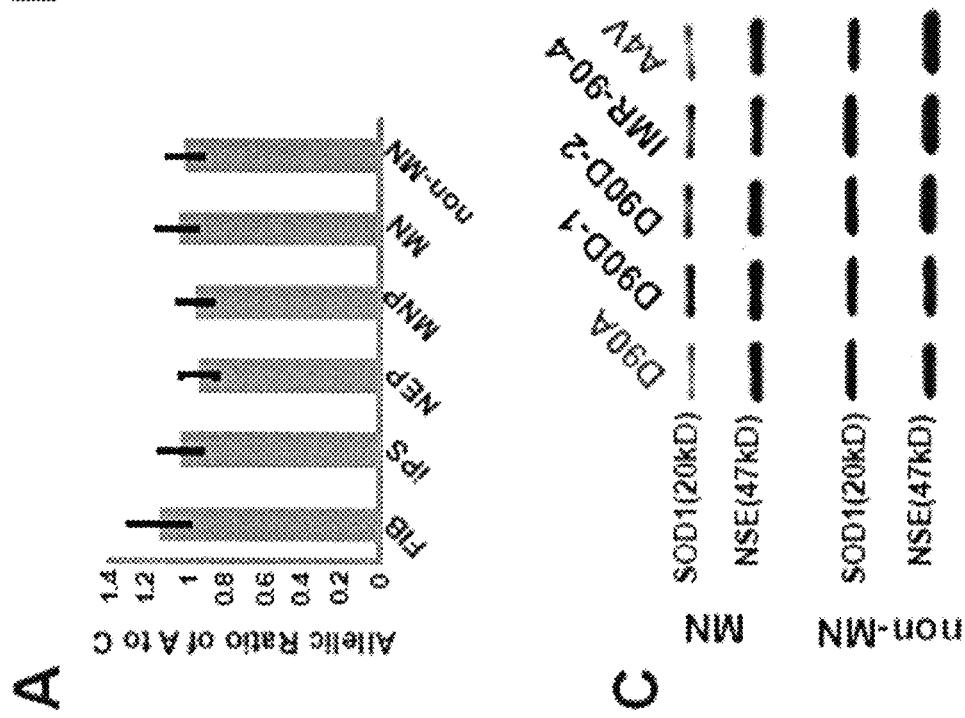
FIGS. 2A-2D demonstrate SOD1 expression and aggregation in iPSC-derived neurons.

The present invention is based, at least in part, on the Inventors' discovery that motor neurons differentiated from induced pluripotent stem cells of ALS patients exhibit phenotypes characteristic of neurodegenerative diseases such as MN-selective accumulation of neurofilament (NF) protein and axonal degeneration. The Inventors further discovered that ALS-iPS cells exhibit altered proportions of NF subunits and significantly reduced levels of NF-low (NF-L). Using induced pluripotent stem (iPS) cells derived from ALS patients, including those with genetic mutations (SOD1 and TDP43) and without genetic mutations (sporadic), the Inventors discovered a motor neuron-selective NF aggregation at early stages and showed that these motor neurons gradually undergo axonal degeneration. They further discovered that ALS motor neurons show reduced expression of neurofilament-low (NF-L) and altered proportion of NF subunits (low, medium and high molecular weight). Importantly, they found that correction of NF-L mRNA expression in motor neurons restores the regular proportion of NF subunits, prevents NF aggregation, and subsequently protects motor neurons from undergoing degeneration.

To date, animal models have failed to fully recapitulate the neuropathology observed in human patients having neurodegenerative diseases. As described herein, ALS-iPS cells retain the ALS disease phenotype and have the capacity for differentiation into neuronal cells that exhibit a phenotype typical of ALS. For example, motor neurons derived from ALS-iPS cells undergo continual degeneration over time. The Examples below disclose that iPS cells generated from a human patient with ALS can be differentiated into motor neurons that then exhibit disease-specific phenotypes and undergo disease-specific cell death in the culture dish. Accordingly, the work described herein represents a very powerful example of a model in which to explore neurodegenerative disease mechanisms and to screen for novel compounds that may attenuate or block neurodegenerative disease processes.

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Methods of the Invention
a. Treatment Methods

One aspect of the present invention relates to methods for treating or preventing a neurodegenerative disease and for protecting against axonal degeneration in a subject in need thereof. As used herein, the terms "treat" and "treating" refer to both therapeutic treatment and prophylactic or preventative measures, wherein the object is to prevent or slow down (lessen) an undesired physiological change or disorder, such as progressive neurodegeneration. For purposes of this invention, beneficial or desired clinical results include, without limitation, an alleviation of one or more clinical indications, decreased motor neuron degeneration, reduced severity of one or more clinical indications, diminishment of the extent of disease, stabilization of the disease state (i.e., not worsening), delay or slowing, halting, or reversing neurodegenerative disease progression, and partial or complete remission, whether detectable or undetectable. "Treatment" also refers to prolonging survival by weeks, months, or years as compared to expected survival if not receiving treatment according to a method provided herein. Subjects in need of treatment can include those already having or diagnosed with a neurodegenerative condition or disorder as well as those prone to, likely to develop, or suspected of having the neurodegenerative condition.

As used herein, the term "neurodegenerative disease" refers to a disease or disorder affecting nerves of the central nervous system that typically manifests as one or a combination of motor, sensory, sensorimotor, or autonomic neural dysfunction. A neurodegenerative disease can be sporadic or genetically acquired, can result from systemic disease or traumatic injury, or can be induced by a neurotoxic agent such as a chemotherapeutic agent. In exemplary embodiments, a neurodegenerative disease appropriate for the present invention is one associated with or characterized, at least in part, by neurofilament (NF) aggregation and neurite degeneration. Neurodegenerative diseases appropriate for the present invention include, without limitation, Parkinson's disease (PD), Alzheimer's disease (AD), Huntington's disease (HD), Spinal Muscle Atrophy (SMA), spinocerebellar ataxias (SCA), Guillain-Barré syndrome (GBS), Parkinson's disease-related disorders, Charcot-Marie-Tooth disease (CMT), amyotrophic lateral sclerosis (ALS), and other motor neuron diseases.

Huntington's Disease (HD) is characterized by progressive neuronal death in different areas of the brain and the appearance of motor coordination deficits and hyperkinetic movement disorders. The spinocerebellar ataxias (SCA) are a group of neurodegenerative diseases characterized by cerebellar ataxia (deficit or failure of muscular coordination), occulomotor abnormalities, upper and lower motor neuron signs, cognitive decline, epilepsy, autonomic dysfunction, sensory deficits, and psychiatric manifestations. See, e.g., Schols et al., Lancet Neurol 3(5):291-304 (2004). Charcot-Marie-Tooth disease (CMT) (also known as Hereditary Motor and Sensory Neuropathy, "HMSN") is the most common inherited disorder of the peripheral nervous system, affecting approximately 1 in 2500 individuals. Clinical subtypes of CMT are associated with progressive distal muscle weakness, atrophy, demyelinating neuropathy (CMT type 1), and axonal loss (CMT type 2).

Amyotrophic lateral sclerosis (ALS) is the most common motor neuron (MN) disease having no effective treatment (Robberecht and Philips, Nat. Rev. Neurosci. 14:248-264 (2013)). A clinical diagnosis of ALS, defined by progressive signs and symptoms of upper and lower motor neuron dysfunction, is typically confirmed using electromyography. Additional tests such as magnetic resonance imaging (MRI) of the brain or spinal column can exclude other diseases. In the absence of treatments to effectively delay or halt disease progression, ALS patient care is largely palliative. While mostly sporadic, some cases of ALS are associated with genetic mutations, among which 20% is caused by mutations in the copper zinc superoxide dismutase (SOD1) gene.

In some cases, the present invention provides a gene therapy method for treating a neurodegenerative disease in a subject in need thereof, where the neurodegenerative disease affects motor neurons or is associated with motor neuron degeneration. The primary goal of gene therapy is to treat a loss-of-function genetic disorder by delivering correcting therapeutic DNA sequences into the nucleus of a cell, whereby long-term expression of such therapeutic DNA sequences at physiologically relevant levels can partially or fully correct the loss-of-function phenotype. Therapeutic gene transfer offers potential advantages over direct administration of a polypeptide systemically or via continuous or targeted production of a target gene product in vivo. Embodiments of the invention comprise delivery of a gene therapy vector having a heterologous gene of interest to obtain stable gene expression in target cells or tissues. The method can include contacting a cell or tissue of a subject in need thereof to a vector comprising a heterologous gene, wherein the vector is introduced into a motor neuron of the subject and wherein expression of the heterologous gene treats the neurodegenerative disease. In some cases, the subject has been diagnosed or is suspected of having amyotrophic lateral sclerosis (ALS) or spinal muscular atrophy of infancy.

As used herein, the phrase "expression of the heterologous gene" refers to expression of a therapeutically effective amount of a heterologous gene in a cell or cells to which the gene therapy vector has been introduced. The "heterologous" gene may be a second copy or an altered copy of a gene that is already part of the subject's genome. Continuous in situ production of physiological concentration of the gene product can provide a therapeutically effective amount of such molecules, thereby treating the neurodegenerative disease. In some cases, the heterologous gene encodes NF-68 (L) protein ("NF-L"). Nucleotide and amino acid sequences for NF-L are set forth as SEQ ID NO:1 and SEQ ID NO:2, respectively. In such cases, introducing a viral gene therapy vector comprising nucleic acid sequence encoding NF-L polypeptide, and targeting the vector to one or more types of neurons, can increase expression of NF-L mRNA and the proportion of NF-L subunit to relative to subunits NF-200 (H) ("NF-H") and NF-145(M) ("NF-M"), whereby the neurodegenerative disease is treated. Nucleotide and amino acid sequences for NF-H are set forth as SEQ ID NO:3 and SEQ ID NO:4, respectively. Nucleotide and amino acid sequences for NF-M are set forth as SEQ ID NO:5 and SEQ ID NO:6, respectively.

Targeted delivery of a therapeutically effective amount of a heterologous gene can treat, prevent, reverse, remove, or compensate for NF aggregation or neurite degeneration in susceptible motor neurons. Accordingly, targeted delivery of a therapeutic gene such as NF-L to vulnerable neurons of the central nervous system or peripheral nervous system can be a useful neuroprotective (e.g., prophylactic) or therapeutic strategy for a subject having, suspected of having, predisposed to developing, or likely to be susceptible to a neurodegenerative disease.

In exemplary embodiments, recombinant nucleic acid sequences are administered in a vector. Vectors appropriate for use according to a method of the present invention include, without limitation, viral vectors, preferably adenoviruses, herpes viruses, adeno-associated viruses (AAV), retroviruses including lentiviruses, poxviridae, baculovirus, vaccinia or Epstein-Barr viruses. In exemplary embodiments, vectors are adenoviruses. Various serotypes of adenovirus are known in the art. For example, an appropriate adenovirus serotype for use according to a method of the present invention can be a type 2 or type 5 human adenovirus (Ad2 or Ad5) or an adenovirus of animal origin (e.g., adenoviruses of bovine, canine, murine, ovine, porcine, avian, and simian origin). In some cases, it is preferable to use replication-defective adenoviruses, comprising at least one non-functional viral region selected from E1, E2 and/or E4. Such adenoviruses may be produced according to conventional methods such as the method described by Dedieu et al., *J. Virology* 71:4626-4637 (1997). Recombinant adenoviruses carrying a replication defective genome can be prepared according to methods known in the art using either competent packaging cells or transient transfection (Graham F. L. and Prevec L., Gene transfer and expression protocols; Manipulation of adenovirus vectors, Methods in Molecular Biology (1991), The Humana Press Inc, Cliften, N.J., chapter 11, pp. 109-128). In some cases, a method of treating a neurodegenerative disease in a subject in need thereof comprises contacting a cell or tissue of a subject to a recombinant adeno-associated virus vector comprising a heterologous gene, wherein the vector is introduced into a neuron (e.g., motor neuron) of the subject and wherein expression of the heterologous gene treats the neurodegenerative disease.

In another aspect, the present invention provides a method of protecting against axonal or neurite degeneration in a subject in need thereof. The method comprises administering one or more recombinant nucleic acid sequences (polynucleotides) encoding a NF-L polypeptide to tissue of the subject, wherein the nucleic acid sequences are targeted to, for example, neurons of the tissue (e.g., motor neurons), and wherein expression of NF-L in targeted neurons protects the motor neurons from neurite degeneration. In some cases, the subject has been diagnosed or is suspected of having ALS or spinal muscular atrophy of infancy. Recombinant nucleic acid sequences can be administered in a vector such as a viral vector or virus-derived vector. Viral vectors appropriate for use according to a method provided herein include, without limitation, adenoviruses, retroviruses, herpes viruses, and adeno-associated viruses. In some cases, a motor neuron-specific promoter can be used to drive expression of a therapeutic target gene such as NF-L. The efficacy of gene therapy may be monitored by clinical assessment as well as measurement of phosphorylated neurofilament levels as reduction of axonal (neurite) degeneration will decrease the release of phosphorylated neurofilament.

b. Diagnostic Methods

In another aspect, the present invention provides a method of diagnosing a subject as having a neurodegenerative disease. The method can comprise detecting neurofilament protein aggregation, neurite degeneration, and/or cell death as an indicator of neurodegenerative disease in the subject. For example, a method of the present invention can comprise (a) obtaining induced pluripotent stem (iPS) cells from somatic cells of a subject, wherein the iPS cells are capable of differentiation into motor neurons; (b) culturing the iPS cells under conditions suitable to differentiate the iPS cells into motor neurons; and (c) detecting neurofilament levels and aggregation or neurite degeneration in the iPS cell-derived motor neurons, where reduced neurofilament levels, or neurofilament aggregation or neurite degeneration indicates that the subject has a neurodegenerative disease.

In exemplary embodiments, the subject is a living human. For example, the subject can be a living human suspected of or at risk for developing a neurodegenerative disorder. Skin biopsy or blood samples can be obtained from such individuals and reprogrammed into motor neurons either directly (Vierbuchen et al., *Nature* 463:1035-1041; Son et al., *Cell Stem Cell* 9:205-218) or indirectly via iPS cells as exemplified herein. An individual's (e.g., human patient) motor neurons can be assayed for reduced levels of NF-L polypeptide or mRNA, increased release of phosphorylated neurofilament to culture media, or neurofilament aggregation, neurite degeneration, susceptibility to stress, or increased cell death. NF-L levels can be assayed using, for example, RT-PCR (for mRNA) or using an anti-NF-L antibody (e.g., Western blot). Release of soluble phosphorylated NF into culture medium can be detected using, for example, an enzyme-linked immunosorbent assay (ELISA). Such assays could be readily performed in a clinical setting. In some cases, diagnosis of an individual suspected of or at risk for developing a neurodegenerative disorder may be validated by detecting increased levels of phosphorylated neurofilament in a cerebral spinal fluid sample obtained from the individual.

c. Screening Methods

In another aspect, the present invention provides methods for identifying candidate therapeutic agents to treat a neurodegenerative disease, to slow or halt neurodegeneration, to alter a neurodegenerative disease mechanism, or to correct an observed neurodegenerative disease phenotype. For example, methods of the present invention can comprise testing compounds for their ability to modify or restore cellular levels of NF-L, to restore cellular proportions of NF subunits, or to attenuate or prevent neurite degeneration. Alternatively, the methods provided herein could identify compounds that promote cell survival (e.g., compounds that stimulate intracellular protective pathways or promote secretion of growth factors) independent of NF function.

In some cases, the present invention provides a method of evaluating a candidate neuroprotective agent, where the method comprises the steps of contacting a candidate neuroprotective agent to motor neurons derived from induced pluripotent stem (iPS) cells obtained from somatic cells of a human amyotrophic lateral sclerosis (ALS) patient, wherein the motor neurons exhibit a phenotype typical of ALS; and evaluating the contacted motor neurons for a neuroprotective effect of the agent. In some embodiments, the method will include evaluating the effect of the agent relative to motor neurons derived from iPS cells obtained from somatic cells of a human ALS patient that have not contacted the agent. A "neuroprotective effect" can include, without limitation, a reduction in severity of neurodegeneration, a delay in onset of neurodegeneration, a reduction in severity of neurofilament (NF) aggregation and neurite degeneration, and increased motor neuron viability in vitro. For example, a compound contacted to an ALS iPS-derived motor neuron culture can alter neurofilament levels, neurofilament subunit proportion, neurofilament aggregation, axonal or neurite degeneration, or cell survival and such effects of the compound can be assayed, selected, and validated. See, for example, Yang et al., *Cell Stem Cell*. (2013) Boyd et al., *J Biomol. Screen*. 19(1):44-56 (2014); Naohiro et al., *Sci. Transl. Med*. 145:104 (2012); Sharma et al., *Methods Enzymol*. 506:331-60 (2012); Burkhardt et al., *Mol. Cell Neurosci*. 56:355-64 (2013).

In some cases, the method can comprise differentiating iPS cells, derived from somatic cells of a human subject, into neurons, preferably as disclosed below, and examining the effect of a test compound on NF subunit proportions or NF-L levels of the motor neurons, where an increase in NF-L protein relative to motor neurons derived from iPS cells from somatic cells of an ALS patient that have not been exposed to the test compound indicates that the compound modifies cellular NF subunit proportions or NF-L levels. As used herein, the phrases "differentiation into neurons" and "differentiating into neurons" refer to promoting the differentiation of iPS cells into cells having the genetic markers, cell function, and cell morphology characteristic of a particular neuronal lineage (e.g., motor neurons, Gabaergic neurons, cholinergic neurons, dopaminergic neurons).

The method can additionally or alternatively comprise examining the effect of a test compound on axonal or neurite degeneration relative to neurons derived from iPS cells from somatic cells of a human subject having a neurodegenerative disease that have not been exposed to the test compound. In some cases, the method comprises examining the effect of a test compound on axonal or neurite degeneration relative to motor neurons derived from iPS cells of a human ALS patient that have not been exposed to the test compound. Such effects on ALS-patient derived motor neurons can be detected by assaying for NF-L protein production, NF-L mRNA levels, degree of neurite degeneration, and onset or extent of cell death. Changes in neurite length are detected as an indicator of neurite degeneration. In exemplary embodiments, neurite length is measured using a reporter system such as the luciferase reporter NanoLuc (Nluc) fused with SYNAPTOPHYSIN (SYP), a synaptic glycoprotein that targets the Nluc reporter to axonal membrane, as described in U.S. Patent Application Ser. No. 62/112,441, filed Feb. 5, 2015 (incorporated herein by reference in its entirety).

In another embodiment, the method includes screening test compounds for an effect on motor neuron survival. Compounds that increase motor neuron cell survival, relative to ALS-patient derived motor neurons that have not been exposed to the test compound, are excellent candidates for further drug testing.

In some cases, the method further comprises obtaining a population of iPS cells derived from somatic cells from human subject known to have a neurodegenerative disease such as ALS. In exemplary embodiments, the somatic cells of an ALS patient are fibroblasts. Other types of somatic cells may also be used, including without limitation, blood cells, hair follicle cells, fat cells, and neural cells. To confirm that reprogramming of wild-type and ALS fibroblasts to a pluripotent state has occurred, one may wish to use standard techniques including, but not limited to, quantitative PCR with reverse transcription (qRT-PCR), teratoma formation, DNA fingerprinting and microarray analysis. Pluripotency criteria have been described (see Chan et al., Live cell imaging distinguishes bona fide human iPS cells from partially reprogrammed cells, *Nat. Biotech.*, 27:1033-1037, 2009). Typically, one would look for teratoma formation and expression of endogenous Oct4, SSEA, TRA, and other markers. One could also assay for the ability of the cells to make embryoid bodies that produce all three dermal lineages.

Compositions of the Invention

In a further aspect, the present invention provides compositions useful for treating a neurodegenerative disease or protecting against neurite degeneration in a subject in need thereof. In particular, the present invention provides recombinant nucleic acid molecules and expression vectors comprising such nucleic acid molecules. In some cases, a recombinant nucleic acid molecule comprises a nucleic acid sequence encoding a NF-L polypeptide (e.g., human NF-L). A recombinant nucleic acid molecule of the invention can further comprise a motor neuron-specific promoter operably linked to a target nucleic acid sequence (e.g., a nucleic acid sequence encoding human NF-L).

In exemplary embodiments, a recombinant nucleic acid molecule of the present invention is in a vector. In some cases, the vector is a plasmid (e.g., plasmid expression vector) or is a virus or virus-derived. For example, the vector can be a virus selected from the following: an adenovirus, a retrovirus, a herpes virus, and an adeno-associated virus. In some cases, the vector is a replication-defective adenovirus vector (e.g., a human replication-defective adenovirus). A replication-defective adenovirus vector is capable of delivering its genome to an infected cell, but comprises one or more disabling mutations that prevent activation of viral early gene expression and DNA replication. For example, the replication-defective adenovirus vector pAdRSVβgal lacks the early region 1 (E1) genes needed to efficiently activate transcription of the other viral early genes, including those encoding viral DNA replication proteins and those responsible for inactivating the cellular DNA damage response. See Stratford-Perrncaudet et al., *J. Clin. Invest.* 90:626-30 (1992).

In another aspect, the present invention provides kits useful for the diagnosis, treatment, or monitoring of a neurodegenerative disease. For example, a kit of the present invention can be used to diagnose or monitor disease progression in a subject predisposed to or suspected of developing a neurodegenerative disease or suffering from a neurodegenerative disease. In some cases, a kit of the present invention can comprise the following components: at least one oligonucleotide primer capable of hybridizing to or amplifying a target NF-L nucleic acid sequence; at least one reference corresponding to a level of NF-L target nucleic acid; at least one buffer or reagent; and a container. By way of example, oligonucleotide primers appropriate for a kit of the present invention include, without limitation, the nucleotide sequences of SEQ ID NO:7 (5'-ATGAGTTCCTTCAGCTACGAGC-3') and SEQ ID NO:8 (5'-CTGGGCATCAACGATCCAGA-3').

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The invention will be more fully understood upon consideration of the following non-limiting Examples.

EXAMPLES

Example 1

Efficient Differentiation of ALS iPS Cells and Genetically Corrected ALS iPS Cells to Motor Neurons Fibroblasts from a 50-year old female carrying the D90A SOD1 mutation (ND29149, P3; Coriell Institute) were reprogrammed using the non-integrating Sendai virus as described (Ban et al., *Proc. Natl. Acad. Sci. U.S.A* 108:

14234-14239 (2011)). A4V SOD1 mutant iPSC lines, established with retrovirus, were obtained from Coriell (ND35671). The IMR-90-4 iPSC line, generated from fetal fibroblasts (Hu et al., 2010), was used as a wild-type (wt) control. The iPS cells reprogrammed with Sendai virus were integration-free as confirmed by qPCR analysis for viral sequences (data not shown). All iPS cells became stable cell lines, exhibited typical morphology, expressed the pluripotency markers including NANOG (FIGS. 1A-B), OCT4, SSEA-4, and SOX2, generated teratomas in vivo, and retained karyotype stability (some data not shown). Human ESCs (H9 line, NIH registry 0046) were used as an additional wt control and as a recipient for transgenic expression of mutant SOD1. The SOD1 D90A mutation was maintained as confirmed by sequencing exon 4 of SOD1 (FIG. 1C, 1D).

To establish isogenic controls under the same genetic and epigenetic background, we corrected the D90A mutation in the iPS cells using TALEN mediated homologous recombination. Transgenes were targeted to the AAVS1 locus in hESCs and iPSCs by TALEN. The donor plasmid for constitutive expression of D90A SOD1 was constructed by replacing the CAG-GFP cassette of the plasmid AAV-CAGGS-EGFP (Addgene, Cambridge, Mass.) with the CAG-D90A SOD1 cassette via SpeI and MluI double digestion. Similarly, the Tet-inducible expression plasmid was constructed by replacing the CAG-GFP cassette with the CAG-Tet-On 3G cassette (pTRE3G-SV40-polyA cassette, Clontech, Mountain View, Calif.) via the SpeI site. NF-L cDNA sequence was inserted into the SalI and MluI sites of the plasmid for conditional NF-L expression. To correct the SOD1 D90A mutation, a 986 basepair (bp) or 829 bp fragment at both sides of the TALEN target point was PCR-amplified using genomic DNA from H9 hESCs. The digested fragments were then cloned into the multiple clone site of plasmid PL452 (Frederick National Lab). TALENs pairs targeting the AAVS1 locus was designed as described (Hockemeyer et al., Nat. Biotechnol. 29:731-734 (2011)). TALEN activity was assayed via surveyor nuclease (Transgenomic, Omaha, Ne.). A standard protocol was used for cellular transfection and cloning as described (Hockemeyer et al., Nat. Biotechnol. 29:731-734 (2011)).

PCR analysis of individual single-cell-derived G418-resistant clones using a primer external to the 5' donor homology region and a primer against the PGK promoter demonstrated disruption of the genomic locus and integration of the donor vector with a frequency of about 45% (data not shown). Two selected clones, designated as D90D1 and D90D2, showed successful correction of the targeted locus, as revealed by TaqMan SNP genotyping assays and by sequencing (FIG. 1C, 1D). The corrected iPSCs displayed a normal karyotype, uniform expression of pluripotency markers, and generation of teratomas, and identical polymorphisms to their parental cells as assayed by short tandem repeat analysis.

Pluripotent stem cells were first differentiated to neuroepithelia in a neural medium consisting of DMEM/F12, N2 supplement, and non-essential amino acids in the presence of SB431542 (2 µM), LDN193189 (300 nM), and CHIR99021 (3 µM; Stemgent) for 7 days. At day 8, the neuroepithelia were treated with RA (0.1 µM) and purmorphamine (0.5 µM) for 7 days for MN induction. For generation of non-MNs, cyclopamine (0.5 µM) was added in place of purmorphamine. At day-14, both MN and non-MN progenitors in the form of rosettes were isolated and expanded as floating clusters in suspension in the same respective medium but without SB431542, LDN193189, and CHIR99021 for an additional 7 days before plating on laminin substrate for generating mature neurons. To generate synchronized post-mitotic neurons, the cultures were treated from day 18-21 with compound E (0.1 µM) to block cell proliferation.

Initial experiments were designed to assay whether MN generation is altered by SOD1 mutations. Using a protocol (FIG. 1E) modified from previous methods (Amoroso et al., J. Neurosci. 33:574-586 (2013)); Li et al., Stem Cells 26:886-893 (2008)), it was determined that both the mutant SOD1 iPSCs (D90A and A4V) and genetically corrected (D90D), as well as wt iPSCs (IMR-90-4), efficiently differentiated into OLIG2$^+$ MN progenitors at day 14, MNX1$^+$ postmitotic MNs at day 21, and CHAT$^+$ maturing MNs by 21-30 days (FIGS. 1F-G), with 94% of the TUJ1$^+$ neurons, or 90% of total differentiated cells being MNX1$^+$ MNs (FIG. 1H-I). These results indicated that ALS mutations do not affect MN development. We also differentiated the iPSCs to spinal neurons that were void of MNX1$^+$ or CHAT$^+$ MNs by blocking hedgehog signaling using cyclopamine during neural patterning (FIG. 1E), which forms a non-MN control within the individual iPSC line. At 4-5 weeks of iPSC differentiation, no glial fibrillary acidic protein (GFAP)-expressing astrocytes were observed (FIG. 1F-G), which is a similar result to previous observations that GFAP-expressing astrocytes do not usually appear until after 2-3 months of hPSC differentiation (Krencik et al., Nat. Biotechnol. 29:528-534 (2011); Serio et al., Proc. Natl. Acad. Sci. U.S.A 110:4697-4702 (2013)). Additionally, we used compound E, a notch signaling inhibitor, to prevent generation of new neurons from progenitors. The highly enriched and synchronized MNs and non-MNs enable phenotypic characterization at cellular and molecular levels.

Example 2

ALS Motor Neurons Exhibit Small Aggregates of Mutant SOD1 and NF Aggregates

Expression of multiple copies of disease-causing mutant SOD1 in animals results in increased expression and aggregation of SOD1 (Bruijn et al., Science 281:1851-1854 (1998); Furukawa et al., Proc. Natl. Acad. Sci. U.S.A. 103:7148-7153 (2006); Karch et al., Proc. Natl. Acad. Sci. U.S.A. 106:7774-9 (2009)). We first asked if SOD1 is comparably expressed in MNs and non-MNs. Western blotting indicated that the SOD1 level in day-30 MNs was approximately 40% lower than that in non-MNs (FIG. 2C). Next, we assayed whether a single copy of mutant SOD1 would alter the level of SOD1 and cause its aggregation in human ALS neurons (neurons of human subjects having ALS). By quantitative PCR (qPCR), it was observed that the ratios between the mutant and wild-type (wt) alleles were about 1 in fibroblasts, iPSCs, neuroepithelia, MN progenitors, MNs, and non-MNs for the D90A mutant, whereas in wt cells both copies were wt (FIG. 2A), indicating that the mutant SOD1 copy is maintained during reprogramming and neural differentiation. By RT-qPCR we then found that mutant SOD1 MNs and non-MNs expressed a similar SOD1 level as wt and genetically corrected ALS cells (FIG. 2B). Interestingly, Western blotting indicated that mutant MNs, but not mutant non-MNs, expressed an even lower level of SOD1 than wt and genetically corrected ALS MNs (FIG. 2C). This unexpected pattern of changes was replicated in six sets of biological samples. Thus, unlike in transgenic animals, the total amount SOD1 protein does not increase in ALS patients' MNs, at least at the age analyzed.

Immunostaining for SOD1 and examination under confocal microscopy showed a ubiquitous expression pattern without discernible aggregates in MNs. We reasoned that aggregates may have been absent or too small to discern under light microscopy. Immuno-electron microscopy (EM) revealed an even distribution of fine gold particles in cytoplasm and neurites of MN cultures from wt and genetically corrected ALS cells. In the ALS MN cultures, clusters of gold particles, averaged 64±5 nm in diameter, were present in cytoplasm, neurites, and nuclei (FIG. 2D). In transgenic animals, SOD1 aggregates are often present on mitochondrial membrane (Bergemalm et al., *J. Neurosci.* 26:4147-4154 (2006); Pasinelli et al., *Neuron* 43:19-30 (2004); Vijayvergiya et al., *J. Neurosci.* 25:2463-2470 (2005)). Careful examination revealed no association of SOD1 aggregates with mitochondria in ALS patients' MNs (FIG. 2D). In the ALS non-MN cultures, there were more gold particles than in MNs, but they were singular, of 10.73±1.07 nm in diameter (FIG. 2D, the fine particles were revealed in non-contrasted image for non-MNs). Thus, small SOD1 aggregates are present in the cytoplasm, nuclei, and neurites but not in mitochondria of ALS MNs.

Figures 3A, 3B, 3C, 3D:
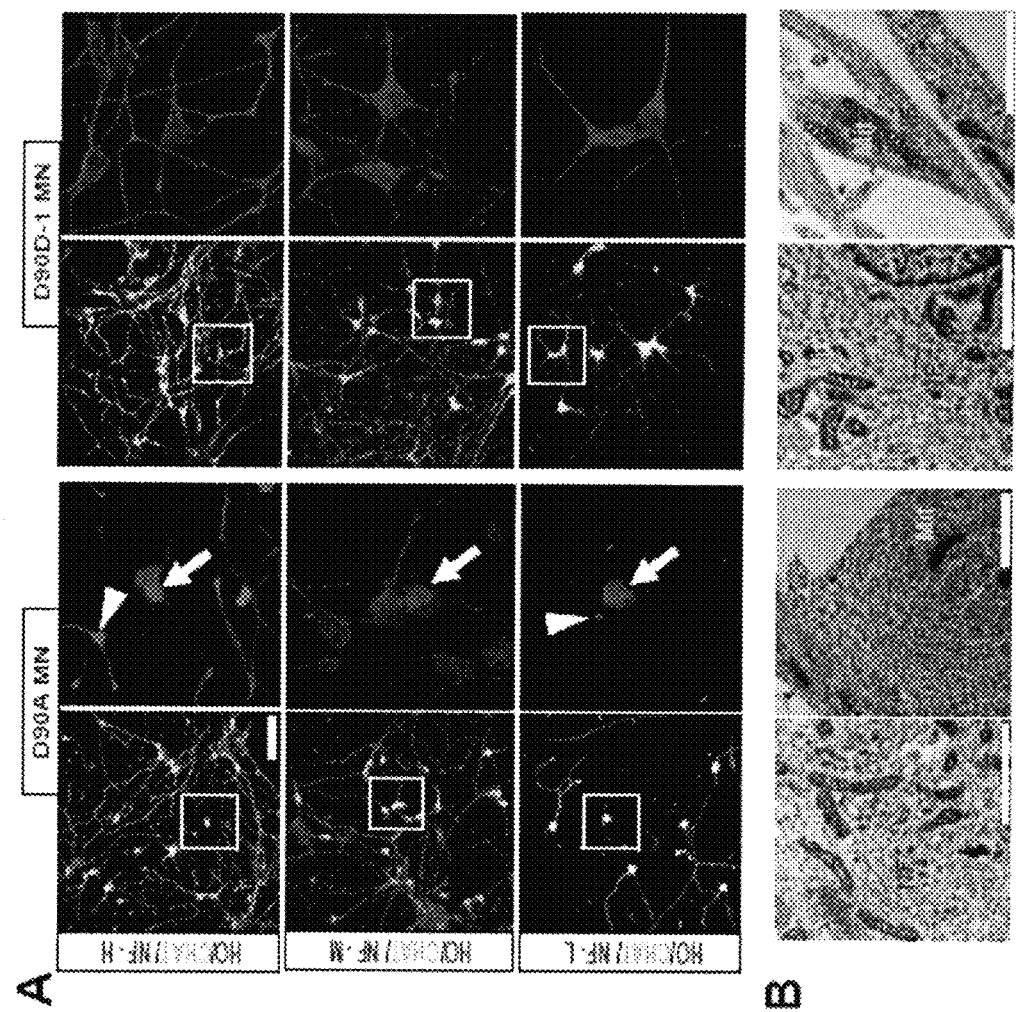
FIGS. 3A-3D depict neurofilament (NF) aggregates in ALS iPSC-derived neurons.

NF aggregates in the perikaryon and proximal axons of spinal MNs is hallmark ALS pathology (Carpenter, *Neurology* 18:841-851 (1968); Hirano et al., *J. Neuropathol. Exp. Neurol.* 43:471-480 (1984)). Immunostaining for NF-200 (H), NF-145(M) and NF-68(L) at day-30 revealed distinct, focal accumulation of immunoreactive products in cytoplasm and neurites of CHAT$^+$ ALS MNs (FIG. 3A). Such NF aggregates were rare in ALS non-MNs or MNs from wt and genetically corrected ALS iPSCs (see FIG. 3A). The aggregates in the cytoplasm and proximal neurites were often accompanied by lower immunofluorescent staining for NF (FIG. 3A) and other proteins (CHAT) in distal neurites. However, the distribution of βIII-tubulin in ALS MN neurites was not altered. The identity of the aggregates was confirmed by electron microscopy, showing disorganized NFs near the nucleus or in the proximal neurite with mitochondria surrounding or inside of the aggregate (FIG. 3B).

NF aggregates were defined as a focal accumulation of immunoreactive products with its intensity being 3 times higher than that in its surroundings. Neurite swelling or beading was defined as an enlargement of a neurite that is at least twice the diameter of the neurite. At least 500 neurites were counted in each group. Statistical analyses were performed using one-way ANOVA (Tukey or Dunnett for multiple comparisons) in SPSS13.0. Quantification of NF aggregates indicated an increasing number of ALS MNs and their neurites that contained NF aggregates at day-24, 27, and 30, or 4, 7, and 10 days after plating day-21 cells for maturation (FIGS. 3C-D). By day-10, over 60% of the MN cell bodies or 25% of neurites contained NF aggregates and the average size of the NF aggregate was 42.4-75.4 μm$^2$ in cell bodies and 1.75-5.53 μm$^2$ in neurites. The wt and genetically corrected ALS MNs also contained an increasing number of NF aggregates over culture but at a significantly less degree, reaching about 20% of the cells and 8% of the neurites. Fewer NF aggregates existed in non-MNs as compared to MNs in the ALS cells. Thus, NF aggregates are preferentially present in ALS MNs and over time more MNs contain aggregates.

In or surrounding the NF aggregates were often accumulation of mitochondria (FIG. 3B). In SOD1 transgenic mice, mitochondria are often swollen or contain vacuous formations (Vijayvergiya et al., *J. Neurosci.* 25:2463-2470 (2005); Gurney et al., *Science* 264:1772-1775 (1994); Wong et al., *Neuron* 14:1105-1116 (1995); Liu et al., *Neuron* 43:5-17 (2004); Bergemalm et al., *J. Neurosci.* 26:4147-4154 (2006)). This, however, was not observed in the ALS human MNs (FIG. 3B) despite the presence of NF aggregates.

Example 3

Neurite Degeneration in ALS Motor Neurons

Figures 4A, 4B, 4C, 4D, 4E, 4F, 4G:
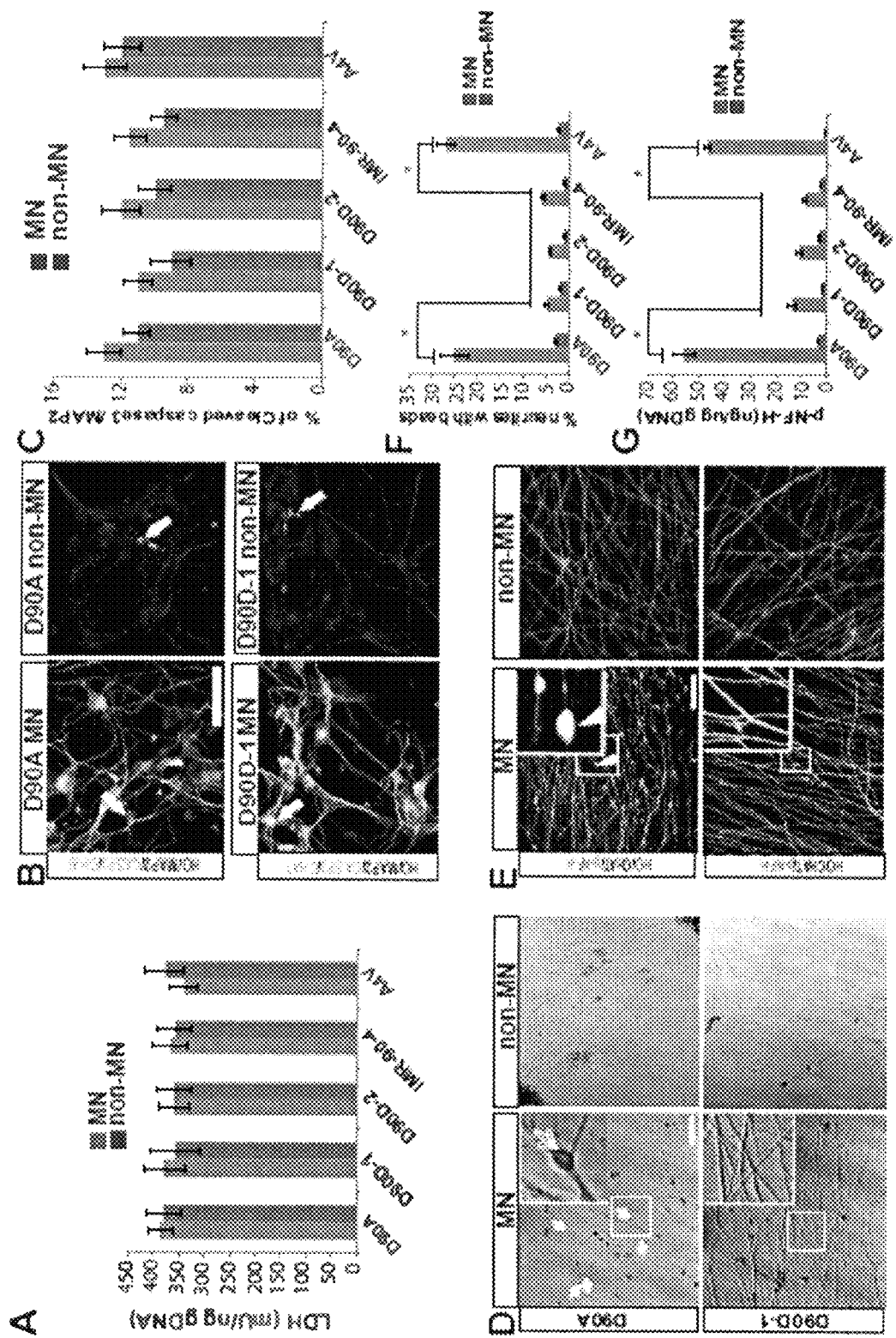
FIGS. 4A-4G depict degenerative changes in ALS MN neurites.

Since ALS MNs contain SOD1 aggregates and NF aggregates, we asked if these neurons undergo degeneration or cell death. Measurement of lactate dehydrogenase (LDH), a soluble enzyme located in cytosol and released during cell death, showed no obvious difference among ALS-, wt-, and corrected-MNs or non-MNs at day-10 (FIG. 4A). Immunostaining for cleaved caspase-3 showed no significant difference among the groups (FIG. 4B). These results suggest that the aggregate-containing MNs are surviving at this stage.

In ALS patients and animals, axons degenerate before symptom onset and MN death (Bruijn et al., *Science* 281: 1851-1854 (1998); Tu et al., *Proc. Natl. Acad. Sci. U.S.A.* 93:3155-3160 (1996); Fischer et al., *Exp. Neurol.* 185:232-240 (2004)). Indeed, we observed bead-like swellings along neurites of ALS MNs under phase contrast microscopy as early as day 7 after plating. At day 10, 25±2.4% neurites in ALS MN cultures exhibited bead-like structures, whereas only 5±0.4% of the neurites had such structures in control MNs (FIGS. 4C, E). Few non-MNs exhibited beading structures (FIG. 4C). Aggregated NF as well as axonal NF is often heavily phosphorylated (Goldstein et al., *Proc. Natl. Acad. Sci. U.S.A.* 80:3101-3105 (1983); Lee et al., *J. Neurosci.* 6:850-858 (1986)). Plasma phosphorylated neurafilament H (p-NF-H) levels closely reflect disease progression and therapeutic response in the SOD1 (G93A) mice and are regarded as an ALS biomarker (Calvo et al., *PLoS. One.* 7:e32632 (2012)). Indeed, immunostaining for p-NF-H showed dense staining in the bead structures in neurites of the ALS MNs, giving a dotted staining appearance as opposed to an even staining pattern in control MNs or non-MNs (FIG. 4D). Similarly, CHAT staining was concentrated in the bead formations (FIG. 4D) as it was weak in other areas of the ALS MN neurites. ELISA measurement of p-NF-H in culture media indicated that its concentration in ALS MNs was 3-6 fold higher than that in the wt and corrected MNs (FIG. 4F). The p-NF-H level in non-MNs across all groups was very low (FIG. 4F). With extended cultures, we observed increased numbers of beads along the neurites and fragmentation of the neurites (not shown), suggesting neurite degeneration at a later stage. These results suggest that axons of ALS MNs undergo degeneration while the cell body is still structurally intact.

Figures 5A, 5B, 5C, 5D, 5E, 5F, 5G:
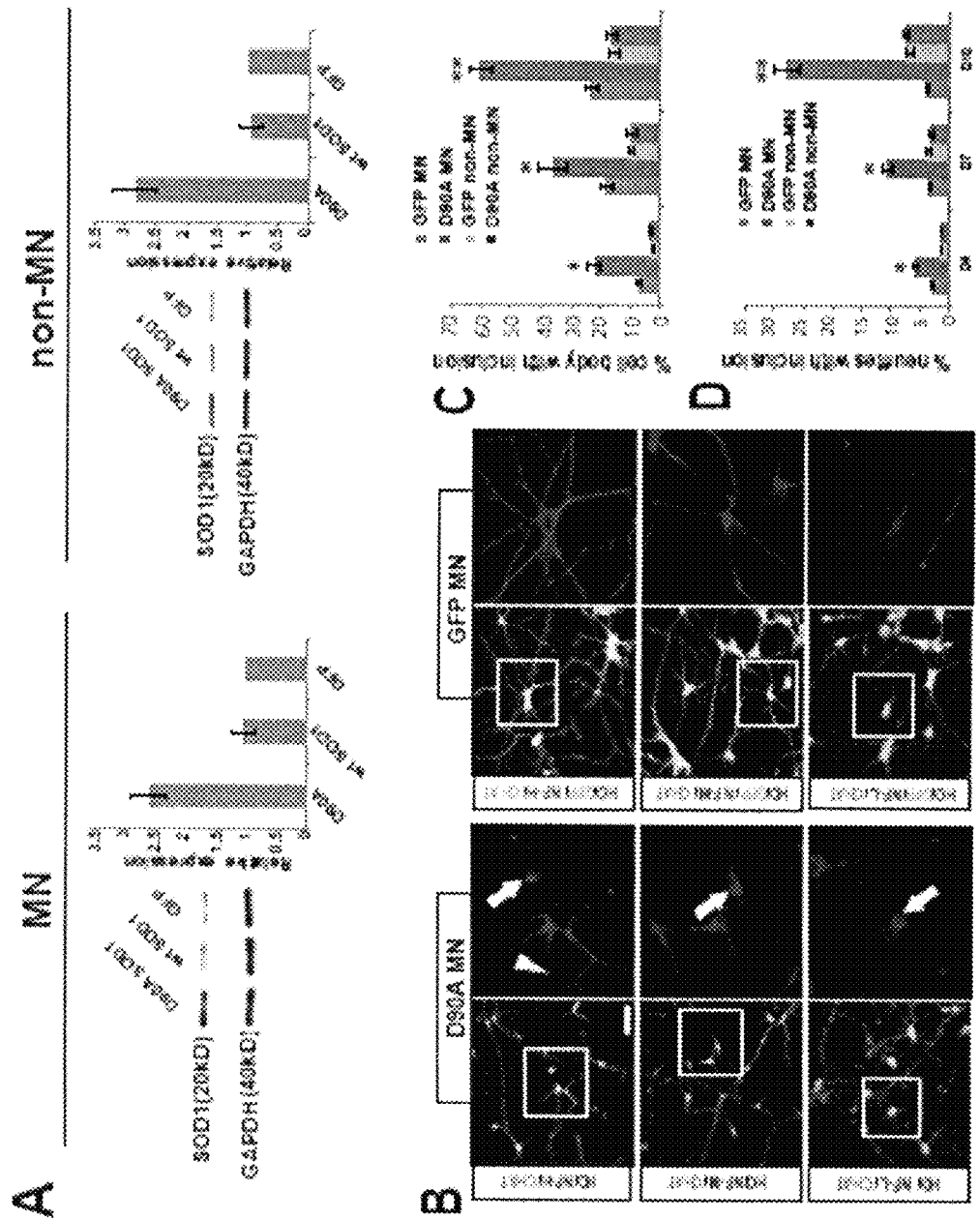
FIGS. 5A-5G present images demonstrating NF aggregation and neurite degeneration in neurons expressing D90A SOD1 in a wild-type (wt) background.

To further establish the cause/effect relationship between mutant SOD1 and the above-described motor neuron pathology, we expressed the D90A mutant SOD1 or EGFP (control) in hESCs (H9 line) in the PPP1R12C (AAVS1) locus by TALEN-mediated homologous recombination. Western blotting revealed a 2.8 fold increase in SOD1 protein in the SOD1-expressing group as compared to the EGFP control group after differentiation of the pluripotent cells to MNs and non-MNs (FIG. 5A). Expression of D90A SOD1 or EGFP did not alter the differentiation of the hESCs to MNs or non-MNs. Similar to the ALS cells, we observed progressively increased numbers of NF aggregates in both cell bodies and neurites of MNs that were derived from the D90A SOD1-expressing, but not EGFP-expressing ESCs over time (FIGS. 5B-D). However, no significant difference in NF aggregates was discerned in non-MNs between the D90A SOD1- and the EGFP-expressing groups (FIGS. 5C-D).

Analysis of neurite degeneration indicated that 90±2% of neurites presented bead-like structures in the D90A SOD1-expressing MNs whereas only 4±0.3% of the MN neurites in the EGFP-expressing group had such formations at day-10 (FIG. 5E). Few non-MNs exhibited beading structures (FIG. 5E). The p-NF-H in culture media was 6 fold higher in D90A-expressing MNs than in the EGFP-expressing MNs. By contrast, p-NF-H was barely detectable in non-MNs (FIG. 5F). Measurement of LDH in the culture media showed no significant difference among all the groups (FIG. 5G). These results indicate that expression of minimal amount of mutant SOD1 (D90A) is sufficient to cause the same disease phenotypes that are seen in cells with naturally occurring mutations.

Example 4

ALS Motor Neurons Exhibit Altered NF Subunit Proportion

Figures 6A, 6B, 6C, 6D, 6E, 6F:
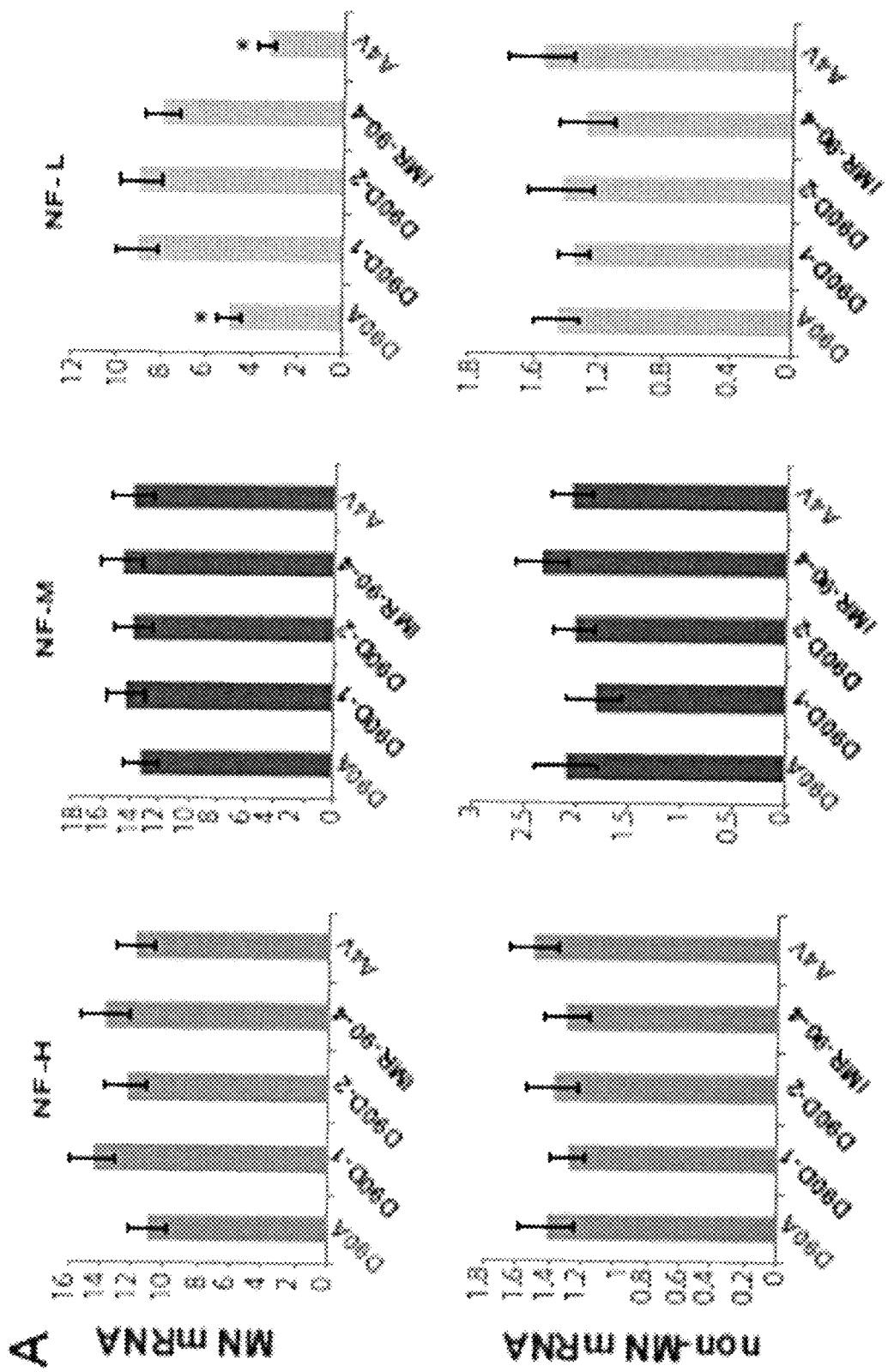
FIGS. 6A-6F present data demonstrating expression of NF subunits in neurons.

Results of the neurite degeneration assays suggest that NF aggregation is an early and key event leading to MN axonal degeneration. NFs are assembled by copolymerization of NF-L, NF-M, and NF-H in a tightly coordinated level (Hoffman and Lasek, *J. Cell Biol.* 66:351-366 (1975)). Transgenic disruption of their balance results in NF aggregation and MN degeneration (Cote et al., *Cell* 73:35-46 (1993); Xu et al., *Cell* 73:23-33 (1993)), resembling ALS pathology. By RT-qPCR analysis, we found no difference in the expression of NF-H and NF-M mRNA between ALS and control (wt and D90D) MNs (FIG. 6A). Interestingly, NF-L mRNA was reduced by 40-60% in ALS MNs as compared to control MNs (FIG. 6A). In non-MNs, however, no obvious difference in all the three NF subunit mRNAs was observed between the disease and control groups (FIG. 6A).

At the protein level, Western blotting revealed that NF-H, NF-M, and NF-L were all decreased in ALS MNs but not in non-MNs as compared to control cells (FIG. 6B). Moreover, NF-L was most prominently downregulated, representing only 30% of the level in wt MNs (FIG. 6B). Because NF-L was downregulated more than the other two subunits, the proportion of NF subunits was altered in ALS MNs but not in non-MNs (FIG. 6C).

Similarly, in the MNs derived from hESCs that express the D90A SOD1, mRNA levels of NF-L, but not NF-H and NF-M, were significantly decreased as compared to controls (expressing EGFP). Strikingly, Western blotting revealed downregulation of NF subunits, especially NF-L, thus altering the proportion of NF subunits in D90A SOD1- but not EGFP-expressing MNs. In contrast, expression of mutant SOD1 or EGFP had no effect on the expression of NF subunits in non-MNs. These results further support the conclusion that mutant SOD1 alters NF compositions.

Figures 7A, 7B, 7C, 7D, 7E, 7F, 7G, 7H:
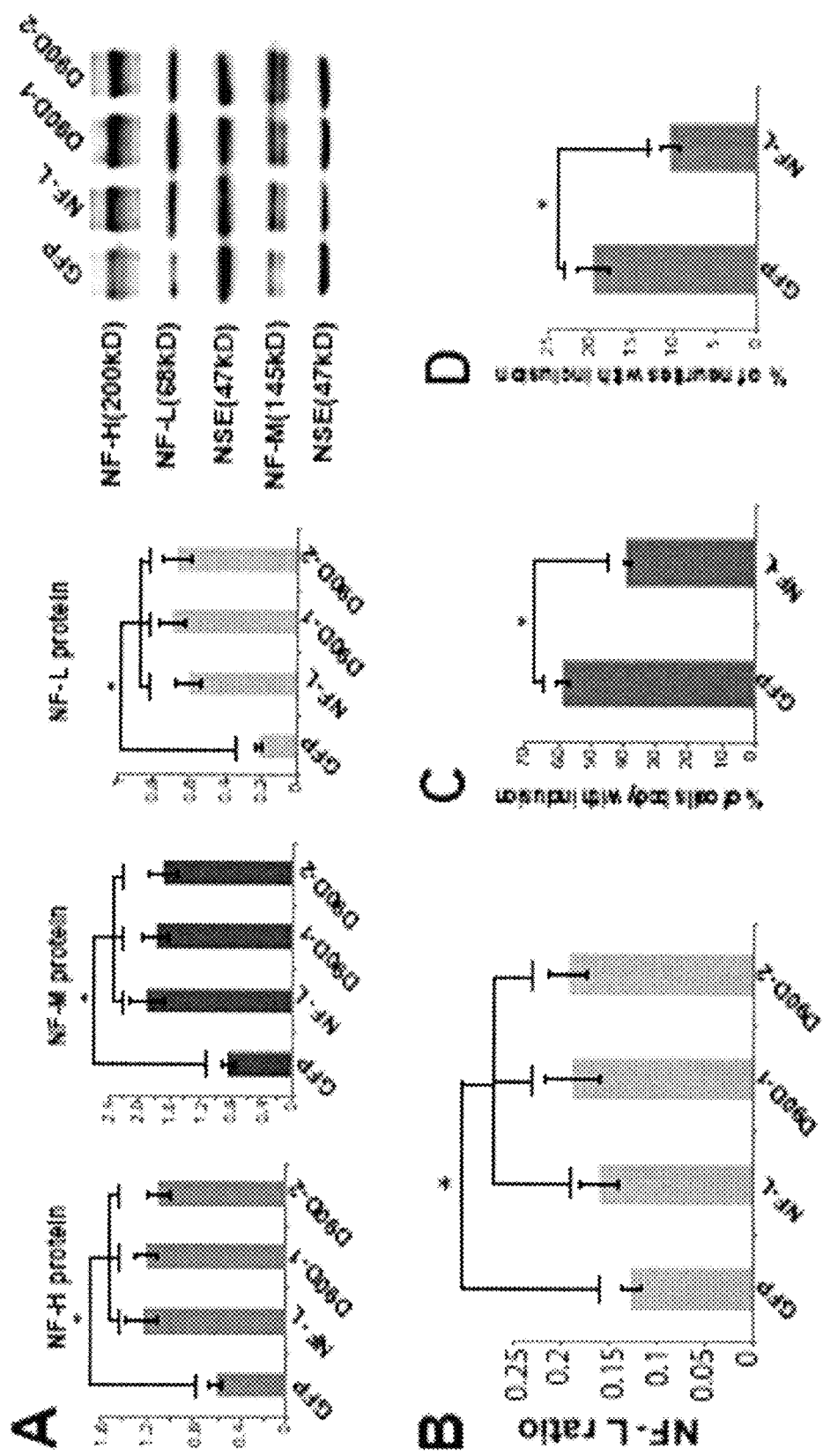
FIGS. 7A-7H present data demonstrating the effects of NF-L expression on NF aggregation and neurite degeneration in ALS MNs.

The above-described results suggest that mutant SOD1 alters the proportion of NF subunits, leading to NF aggregation and neurite degeneration. To test this hypothesis, we conditionally expressed NF-L or EGFP (control) in the PPP1R12C locus of D90A iPSCs by TALEN-mediated homologous recombination. As indicated by dose-dependent changes in EGFP intensity, the expression level of NF-L was increased in a dose-dependent manner when doxycycline (DOX) was added to the MN cultures at day-21, as shown by Western blotting. Remarkably, induction of exogenous NF-L, but not EGFP in the ALS MNs, not only increased the expression of NF-L, but also NF-H and NF-M, to the level comparable to that in corrected MNs (FIG. 7A). At 1 µg/ml DOX, the ratio of NF-L was close to that in wt or genetically corrected MNs (FIG. 7B). Importantly, the NF-L-expressing ALS MNs exhibited fewer NF aggregates in both cytoplasm and neurites at day-10 after plating when compared to the EGFP-expressing ALS MNs, with approximately 30% and 50% reductions in cytoplasm and neurites, respectively (FIGS. 7C-D). Similarly, the proportion of bead-containing MN neurites was 12% in the NF-L-expressing group as compared to 25% in the GFP-expressing group even though it was still higher than that in the genetically corrected group (FIGS. 7E, G). The p-NF-H in culture media in the NF-L-expressing ALS MNs was significantly lower than in the GFP-expressing ALS MNs (FIG. 7H). Together, these results indicate that induction of NF-L in ALS MNs largely restores NF subunit proportion, reduces NF aggregation, and mitigates neurite degeneration.

NF accumulation has been observed in ALS patients and transgenic animals (Carpenter, *Neurology* 18:841-851 (1968); Hirano et al., *J. Neuropathol. Exp. Neurol.* 43:471-480 (1984); Bruijn et al., *Science* 281:1851-1854 (1998); Tu et al., *Proc. Natl. Acad. Sci. U.S.A.* 93:3155-3160 (1996), and transgenic alteration of NFs in neurons can cause ALS-like pathology (Cote et al., *Cell* 73:35-46 (1993); Xu et al., *Cell* 73:23-33 (1993)). Such similarity has led to a hypothesis that altered stoichiometry of neuronal intermediate filaments results in ALS pathology (Julien and Kriz, *Biochim. Biophys. Acta* 1762:1013-1024 (2006)). Using gain-of-function (e.g., expressing mutant SOD1 in hESCs) and loss-of-function (e.g., genetic correction of D90A SOD1 mutation) analyses, we have now established unequivocally that mutant SOD1 leads to NF aggregation. The sequential appearance of NF aggregation and neurite degeneration and especially the mitigation of neurite degeneration following prevention of NF aggregation strongly suggest that NF disorganization triggers the cascade of events, leading to axonal degeneration in ALS MNs.

Figures 6A, 6B, 6C, 6D, 6E, 6F:
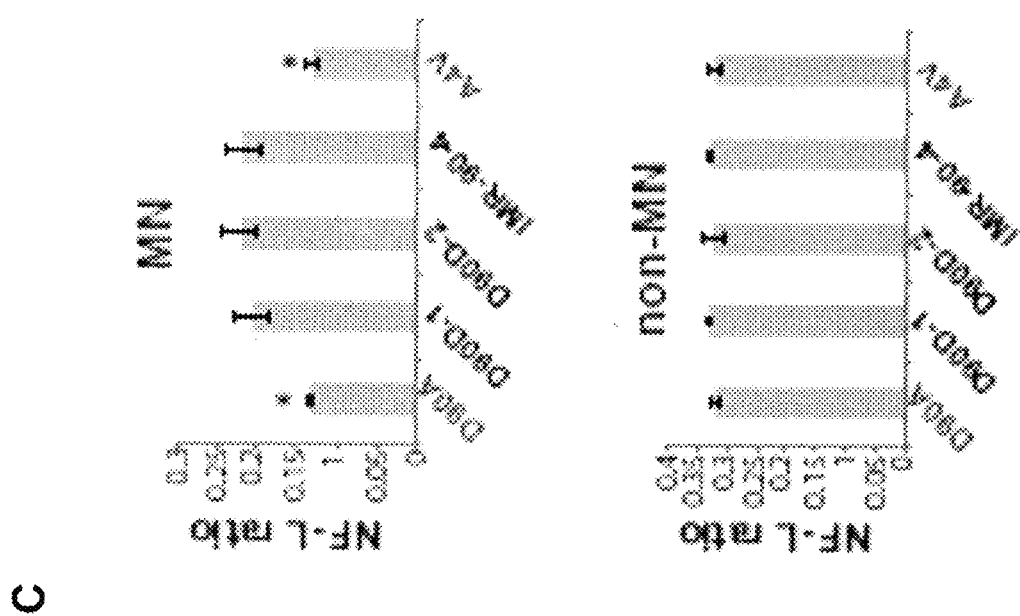

The key question is how NFs are disorganized in ALS MNs, leading to aggregation. It is known that over-expression of NF-H or NF-L leads to NF aggregation (Cote et al., *Cell* 73:35-46 (1993); Xu et al., *Cell* 73:23-33 (1993)), highlighting the importance of correct proportion of NF components for their physiological polymerization. In ALS patients, NF subunit proportion may be altered as there was one report showing a 60% reduction in NF-L mRNAs in MNs using in situ hybridization (Bergeron et al., *J. Neuropathol. Exp. Neurol.* 53:221-230 (1994)) although no information is available whether the protein levels of NF subunits are altered. Strikingly, we observed a significant and specific reduction of NF-L but not NF-H or NF-M mRNA in mutant MNs. At the protein level, all NF subunits are downregulated but the NF-L is most significantly reduced to less than one-third of the level in wild-type MNs. Thus, it is the downregulation of NFs and perhaps more importantly the altered proportion of NF subunits that result in NF aggregation. This may appear counterintuitive as MNs contain substantially higher amount of NFs than non-MNs (see FIG. 6) and it is NF over-expression that results in NF aggregation and axonal degeneration in transgenic animals (Cote et al., *Cell* 73:35-46 (1993); Xu et al., *Cell* 73:23-33 (1993)). Our present study demonstrates that when the proportion of NF subunits is restored by conditionally upregulating NF-L, NF aggregation and even neurite degeneration are significantly mitigated in ALS MNs. We, therefore, propose that alteration of NF subunit proportion in ALS MNs leads to NF aggregation, which is a critical early step toward axonal degeneration.

Example 5

NF Aggregation and NF-L mRNA Down-Regulation in Sporadic ALS MNs

Figures 8A, 8B, 8C:
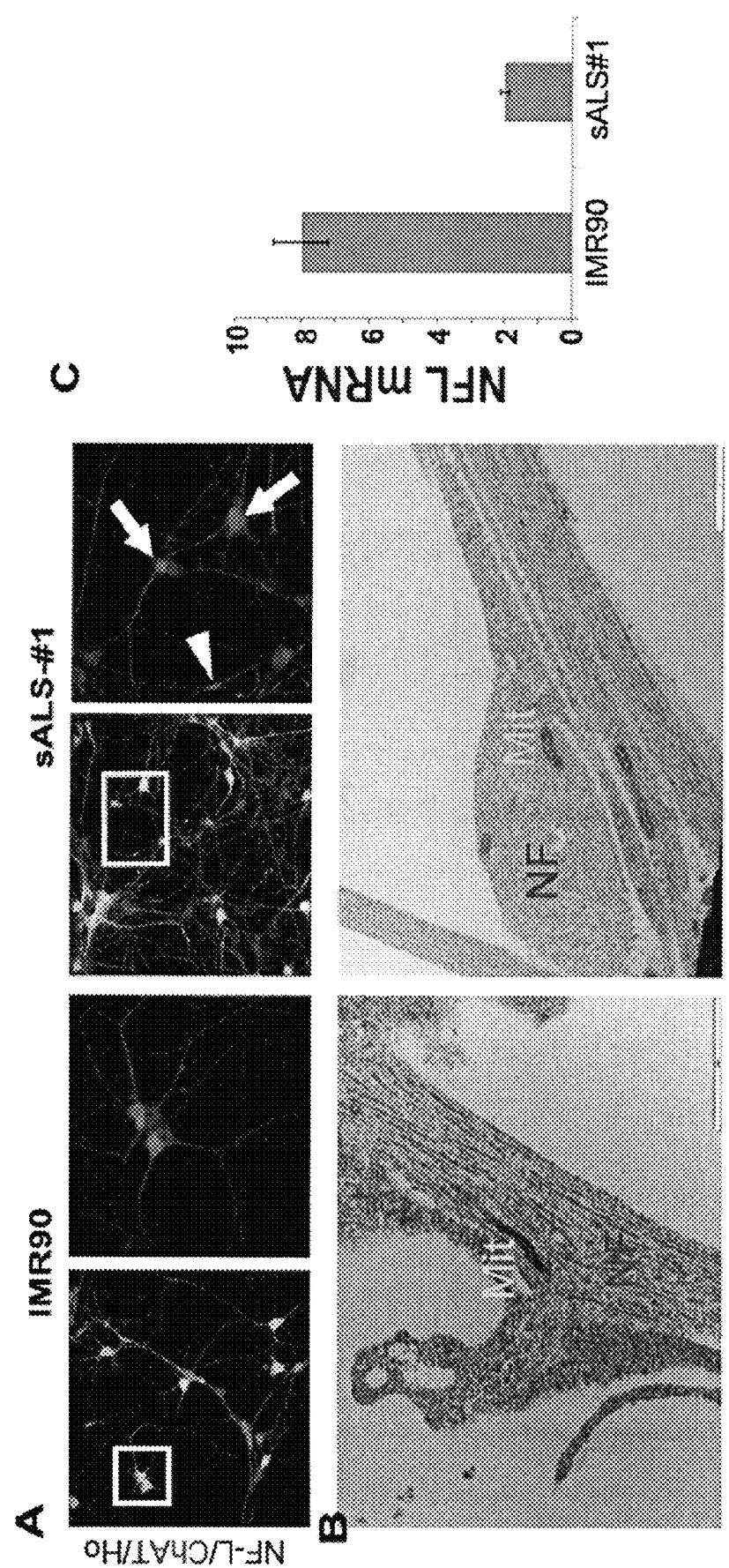
FIGS. 8A-8C present data to demonstrate that sporadic ALS motor neurons exhibit NF aggregates and changes in NF-L mRNA levels.

Skin fibroblasts were collected from 3 sporadic ALS patients who do not have familial history of ALS. Induced PSC lines were obtained from the ALS patients' fibroblasts using non-integrating Sendai virus. Differentiation of the ALS lines indicated that MNs and non-MNs can be generated efficiently. Immunohistochemical staining for NF-H, NF-M, and NF-L showed NF aggregations in MNs but not in non-MNs (FIG. 8), highlighting the recapitulation of disease hallmarks by the iPSC model. RT-qPCR analysis indicated that NF-L mRNA, but not NF-H mRNA or NF-M mRNA, was down-regulated in MNs but not in non-MNs that were differentiated from sporadic ALS iPSCs for 31 days (day-10 after plating day-21 cells) (FIG. 8, MN data are shown). Such a striking similarity to the phenotypes observed in SOD1 familial ALS MNs highlights a common mechanism underlying MN degeneration.

Example 6

Figures 12A, 12B, 12C, 12D, 12E, 12F:
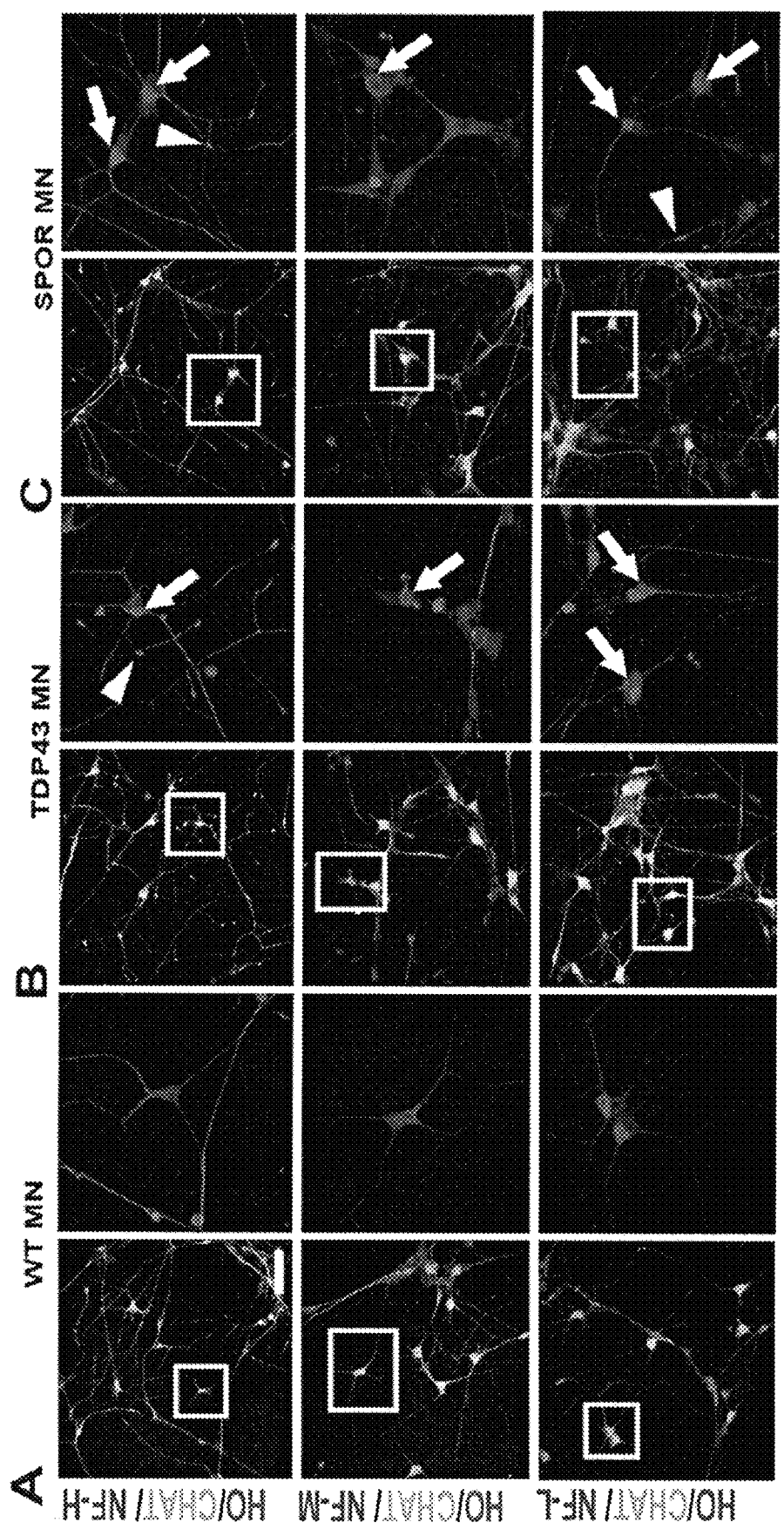
FIGS. 12A-12F present immunofluorescent images of NF-H, NF-M, and NF-L in CHAT$^+$ motor neurons (MNs) and CHAT$^-$ non-MN from wild-type (FIGS. 12A, D), TDP43 mutant (FIGS. 12B, E), and sporadic ALS subjects (FIGS. 12C, F). Staining in the insets is magnified on the right panel. Arrows indicate NF inclusions in the cell body; arrowheads indicate NF inclusions in neurites. Scale bar=50 μm.

NF Aggregates Observed in MNs from Sporadic ALS Subjects and ALS Subjects Having a TDP43 Mutation To determine if NF aggregation occurs in ALS patients with other mutations or those without known genetic defects, we established iPSCs from a patient with TDP43 (TAR DNA-binding protein 43) mutation (G298S) and two sporadic ALS patients (no known genetic defects) Sendai virus. As seen with SOD1 mutant ALS cells, iPSCs from TDP43 or sporadic ALS patients differentiated to motor neurons with similar efficiency. Interestingly, immunostaining for NF-H, NF-M and NF-L indicated that the both TDP43 and sporadic ALS MNs contained distinct, inclusion-like focal accumulation of immunoreactive products (FIG. 12). The aggregates were present both in cell body and neurites. The number of NF inclusions in both cell body and on neurites increased over time. The rates of neurofilament aggregation were significantly higher in ALS MNs compared to that in non-ALS MNs ($P<0.05$) (FIG. 12). The average size of each NF inclusion was approximately $2.94-3.72 \times 10^{-4}$ mm$^2$ in cell bodies and approximately $3.75-5.53 \times 10^{-6}$ mm$^2$ in neurites at Day 10.

Together, these data demonstrate that NF aggregation is a common motor neuron pathology to all ALS patients (those having genetic defects and those without known genetic defects). These data also suggest there is a common underlying mechanism for ALS pathogenesis.

SEQUENCE LISTING

This specification hereby incorporates by reference the material in the ASCII text file submitted herewith, the file name of the ASCII text file is "960296_01827_ST25.txt", created on Mar. 8, 2015, and having a size of 31.3 kilobytes.

We claim:

1. A method for treating a neurodegenerative disease in a human subject in need thereof, the method comprising, in order,
   introducing into a motor neuron of said human subject a viral or virus-derived vector comprising a heterologous gene encoding neurofilament light (NF-L), wherein the heterologous gene comprises SEQ ID NO:1, and wherein expression of NF-L from said introduced vector in said motor neuron treats the neurodegenerative disease, wherein the neurodegenerative disease is amyotrophic lateral sclerosis (ALS); and
   detecting a level of phosphorylated neurofilament in a cerebrospinal fluid sample of said human subject, wherein a decrease in the level following introduction of the viral or virus-derived vector, relative to a level of phosphorylated neurofilament detected prior to the introducing step, indicates treatment of the neurodegenerative disease.

* * * * *

SEQUENCE LISTING

```
<160> NUMBER OF SEQ ID NOS: 8

<210> SEQ ID NO 1
<211> LENGTH: 1632
<212> TYPE: DNA
<213> ORGANISM: Homo sapiens

<400> SEQUENCE: 1
atgagttcct tcagctacga gccgtactac tcgacctcct acaagcggcg ctacgtggag      60
acgccccggg tgcacatctc cagcgtgcgc agcggctaca gcaccgcacg ctcagcttac     120
tccagctact cggcgccggt gtcttcctcg ctgtccgtgc gccgcagcta ctcctccagc     180
tctggatcgt tgatgcccag tctggagaac ctcgacctga gccaggtagc cgccatcagc     240
aacgacctca agtccatccg cacgcaggag aaggcgcagc tccaggacct caatgaccgc     300
ttcgccagct tcatcgagcg cgtgcacgag ctggagcagc agaacaaggt cctggaagcc     360
gagctgctgg tgctgcgcca gaagcactcc gagccatccc gcttccgggc gctgtacgag     420
caggagatcc gcgacctgcg cctggcggcg gaagatgcca ccaacgagaa gcaggcgctc     480
cagggcgagc gcgaagggct ggaggagacc ctgcgcaacc tgcaggcgcg ctatgaagag     540
gaggtgctga gccgcgagga cgccgagggc cggctgatgg aagcgcgcaa aggcgccgac     600
gaggcggcgc tcgctcgcgc cgagctcgag aagcgcatcg acagcttgat ggacgaaatc     660
tcttttctga agaaagtgca cgaagaggag atcgccgaac tgcaggcgca gatccagtac     720
gcgcagatct ccgtggagat ggacgtgacc aagcccgacc tttccgccgc gctcaaggac     780
atccgcgcgc agtacgagaa gctggccgcc aagaacatgc agaacgctga ggaatggttc     840
aagagccgct tcaccgtgct gaccgagagc gccgccaaga caccgacgc cgtgcgcgcc     900 gccaaggacg aggtgtccga gagccgtcgt ctgctcaagg ccaagaccct ggaaatcgaa     960
gcatgccggg gcatgaatga agcgctggag aagcagctgc aggagctgga ggacaagcag    1020
```

```
aacgccgaca tcagcgctat gcaggacacg atcaacaaat tagaaaatga attgaggacc    1080
acaaagagtg aaatggcacg atacctaaaa gaataccaag acctcctcaa cgtgaagatg    1140
gctttggata ttgagattgc agcttacagg aaactcttgg aaggcgagga gacccgactc    1200
agtttccaca gcgtgggaag cataaccagt ggctactccc agagctccca ggtctttggc    1260
cgatctgcct acggcggttt acagaccagc tcctatctga tgtccacccg ctccttcccg    1320
tcctactaca ccagccatgt ccaagaggag cagatcgaag tggaggaaac cattgaggct    1380
gccaaggctg aggaagccaa ggatgagccc ccctctgaag gagaagccga ggaggaggag    1440
aaggacaagg aagaggccga ggaagaggag gcagctgaag aggaagaagc tgccaaggaa    1500
gagtctgaag aagcaaaaga agaagaagaa ggaggtgaag gtgaagaagg agaggaaacc    1560
aaagaagctg aagaggagga gaagaaagtt gaaggtgctg ggaggaacag cagctaag     1620 aagaaagatt ga                                                        1632
```

<210> SEQ ID NO 2
<211> LENGTH: 543
<212> TYPE: PRT
<213> ORGANISM: Homo sapiens

<400> SEQUENCE: 2

```
Met Ser Ser Phe Ser Tyr Glu Pro Tyr Tyr Ser Thr Ser Tyr Lys Arg
1               5                   10                  15

Arg Tyr Val Glu Thr Pro Arg Val His Ile Ser Ser Val Arg Ser Gly
                20                  25                  30

Tyr Ser Thr Ala Arg Ser Ala Tyr Ser Ser Tyr Ser Ala Pro Val Ser
            35                  40                  45

Ser Ser Leu Ser Val Arg Arg Ser Tyr Ser Ser Ser Gly Ser Leu
        50                  55                  60

Met Pro Ser Leu Glu Asn Leu Asp Leu Ser Gln Val Ala Ala Ile Ser
65                  70                  75                  80

Asn Asp Leu Lys Ser Ile Arg Thr Gln Glu Lys Ala Gln Leu Gln Asp
                85                  90                  95

Leu Asn Asp Arg Phe Ala Ser Phe Ile Glu Arg Val His Glu Leu Glu
            100                 105                 110

Gln Gln Asn Lys Val Leu Glu Ala Glu Leu Leu Val Leu Arg Gln Lys
        115                 120                 125

His Ser Glu Pro Ser Arg Phe Arg Ala Leu Tyr Glu Gln Glu Ile Arg
    130                 135                 140

Asp Leu Arg Leu Ala Ala Glu Asp Ala Thr Asn Glu Lys Gln Ala Leu
145                 150                 155                 160

Gln Gly Glu Arg Glu Gly Leu Glu Glu Thr Leu Arg Asn Leu Gln Ala
                165                 170                 175

Arg Tyr Glu Glu Glu Val Leu Ser Arg Glu Asp Ala Glu Gly Arg Leu
            180                 185                 190

Met Glu Ala Arg Lys Gly Ala Asp Glu Ala Ala Leu Ala Arg Ala Glu
        195                 200                 205

Leu Glu Lys Arg Ile Asp Ser Leu Met Asp Glu Ile Ser Phe Leu Lys
    210                 215                 220

Lys Val His Glu Glu Glu Ile Ala Glu Leu Gln Ala Gln Ile Gln Tyr
225                 230                 235                 240

Ala Gln Ile Ser Val Glu Met Asp Val Thr Lys Pro Asp Leu Ser Ala
                245                 250                 255
```

-continued

```
Ala Leu Lys Asp Ile Arg Ala Gln Tyr Glu Lys Leu Ala Ala Lys Asn
            260                 265                 270

Met Gln Asn Ala Glu Glu Trp Phe Lys Ser Arg Phe Thr Val Leu Thr
        275                 280                 285

Glu Ser Ala Ala Lys Asn Thr Asp Ala Val Arg Ala Ala Lys Asp Glu
    290                 295                 300

Val Ser Glu Ser Arg Arg Leu Leu Lys Ala Lys Thr Leu Glu Ile Glu
305                 310                 315                 320

Ala Cys Arg Gly Met Asn Glu Ala Leu Glu Lys Gln Leu Gln Glu Leu
                325                 330                 335

Glu Asp Lys Gln Asn Ala Asp Ile Ser Ala Met Gln Asp Thr Ile Asn
            340                 345                 350

Lys Leu Glu Asn Glu Leu Arg Thr Thr Lys Ser Glu Met Ala Arg Tyr
        355                 360                 365

Leu Lys Glu Tyr Gln Asp Leu Leu Asn Val Lys Met Ala Leu Asp Ile
    370                 375                 380

Glu Ile Ala Ala Tyr Arg Lys Leu Leu Glu Gly Glu Glu Thr Arg Leu
385                 390                 395                 400

Ser Phe Thr Ser Val Gly Ser Ile Thr Ser Gly Tyr Ser Gln Ser Ser
                405                 410                 415

Gln Val Phe Gly Arg Ser Ala Tyr Gly Gly Leu Gln Thr Ser Ser Tyr
            420                 425                 430

Leu Met Ser Thr Arg Ser Phe Pro Ser Tyr Tyr Thr Ser His Val Gln
        435                 440                 445

Glu Glu Gln Ile Glu Val Glu Glu Thr Ile Glu Ala Ala Lys Ala Glu
    450                 455                 460

Glu Ala Lys Asp Glu Pro Pro Ser Glu Gly Glu Ala Glu Glu Glu Glu
465                 470                 475                 480

Lys Asp Lys Glu Glu Ala Glu Glu Glu Ala Glu Glu Glu Glu
                485                 490                 495

Ala Ala Lys Glu Glu Ser Glu Glu Ala Lys Glu Glu Glu Gly Gly
            500                 505                 510

Glu Gly Glu Glu Gly Glu Glu Thr Lys Glu Ala Glu Glu Glu Glu Lys
        515                 520                 525

Lys Val Glu Gly Ala Gly Glu Glu Gln Ala Ala Lys Lys Lys Asp
    530                 535                 540

<210> SEQ ID NO 3
<211> LENGTH: 3063
<212> TYPE: DNA
<213> ORGANISM: Homo sapiens

<400> SEQUENCE: 3
atgatgagct tcggcggcgc ggacgcgctg ctgggcgccc cgttcgcgcc gctgcatggc      60
ggcggcagcc tccactacgc gctagcccga aagggtggcg caggcgggac gcgctccgcc     120
gctggctcct ccagcggctt ccactcgtgg acacggacgt ccgtgagctc cgtgtccgcc     180
tcgcccagcc gcttccgtgg cgcaggcgcc ggctcaagca ccgactcgct ggacacgctg     240
agcaacgggc cggagggctg catggtggcg gtggccacct cacgcagtga aaggagcag      300 ctgcaggcgc tgaacgaccg cttcgccggg tacatcgaca aggtgcggca gctggaggcg     360
cacaaccgca gcctggaggg cgaggctgcg gcgctgcggc agcagcaggc gggccgctcc     420
gctatgggcg agctgtacga gcgcgaggtc cgcgagatgc gcggcgcggt gctgcgcctg     480
ggcgcggcgc gcggtcagct acgcctggag caggagcacc tgctcgagga catcgcgcac     540
```

```
gtgcgccagc gcctagacga cgaggcccgg cagcgagagg aggccgaggc ggcggcccgc      600
gcgctggcgc gcttcgcgca ggaggccgag gcggcgcgcg tggacctgca gaagaaggcg      660
caggcgctgc aggaggagtg cggctacctg cggcgccacc accaggaaga ggtgggcgag      720
ctgctcggcc agatccaggg ctccggcgcc gcgcaggcgc agatgcaggc cgagacgcgc      780
gacgccctga gtgcgacgt gacgtcggcg ctgcgcgaga ttcgcgcgca gcttgaaggc      840
cacgcggtgc agagcacgct gcagtccgag gagtggttcc gagtgaggct ggaccgactg      900
tcggaggcag ccaaggtgaa cacagacgct atgcgctcag cgcaggagga gataactgag      960
taccggcgtc agctgcaggc caggaccaca gagctggagg cactgaaaag caccaaggac     1020
tcactggaga ggcagcgctc tgagctggag gaccgtcatc aggccgacat tgcctcctac     1080
caggaagcca ttcagcagct ggacgctgag ctgaggaaca ccaagtggga gatggccgcc     1140
cagctgcgag ataccagga cctgctcaat gtcaagatgg ctctggatat agagatagcc     1200
gcttacagaa aactcctgga aggtgaagag tgtcggattg gctttggccc aattcctttc     1260
tcgcttccag aaggactccc caaaattccc tctgtgtcca ctcacataaa ggtgaaaagc     1320
gaagagaaga tcaaagtggt ggagaagtct gagaaagaaa ctgtgattgt ggaggaacag     1380
acagaggaga cccaagtgac tgaagaagtg actgaagaag aggagaaaga ggccaaagag     1440
gaggagggca aggaggaaga aggggtgaa gaagaggagg cagaagggg agaagaagaa     1500 acaaagtctc ccccagcaga gaggctgca tccccagaga aggaagccaa gtcaccagta     1560
aaggaagagg caaagtcacc ggctgaggcc aagtccccag agaaggagga agcaaaatcc     1620
ccagccgaag tcaagtcccc tgagaaggcc aagtctccag caaaggaaga ggcaaagtca     1680
ccgcctgagg ccaagtcccc agagaaggag gaagcaaaat ctccagctga ggtcaagtcc     1740
cccgagaagg ccaagtcccc agcaaaggaa gaggcaaagt caccggctga ggccaagtct     1800
ccagagaagg ccaagtcccc agtgaaggaa gaagcaaagt caccggctga ggccaagtcc     1860
ccagtgaagg aagaagcaaa atctccagct gaggtcaagt ccccggaaaa ggccaagtct     1920
ccaacgaagg aggaagcaaa gtcccctgag aaggccaagt ccccagagaa ggaagaggcc     1980
aagtcccctg agaaggccaa gtcccagtg aaggcagaag caaagtcccc tgagaaggcc     2040
aagtccccag tgaaggcaga agcaaagtcc ctgagaaggg ccaagtcccc agtgaaggaa     2100
gaagcaaagt cccctgagaa ggccaagtcc ccagtgaagg aagaagcaaa gtccctgag     2160 aaggccaagt cccagtgaa ggaagaagca aagacccccg agaaggccaa gtccccagtg     2220
aaggaagaag ctaagtcccc agagaaggcc aagtccccag agaaggccaa gactcttgat     2280
gtgaagtctc cagaagccaa gactccagcg aaggaggaag caaggtcccc tgcagacaaa     2340
ttccctgaaa aggccaaaag ccctgtcaag gaggaggtca agtccccaga gaaggcgaaa     2400
tctcccctga ggaggatgc caaggcccct gagaaggaga tcccaaaaaa ggaagaggtg     2460
aagtccccag tgaaggagga ggagaagccc caggaggtga agtcaaagag ccccccaaag     2520
aaggcagagg aagagaaagc ccctgccaca ccaaaaacag aggagaagaa ggacagcaag     2580
aaagaggagg cacccaagaa ggaggctcca aagcccaagg tggaggagaa gaaggaacct     2640
gctgtcgaaa gcccaaaga atccaaagtt gaagccaaga aggaagaggc tgaagataag     2700
aaaaaagtcc caccccaga gaaggaggct cctgccaagg tggaggtgaa ggaagacgct     2760
aaacccaaag aaaagacaga ggtagccaag aaggaaccag atgatgccaa ggccaaggaa     2820
cccagcaaac cagcagagaa gaaggaggca gcaccggaga aaaaagacac caaggaggag     2880
```

```
aaggccaaga agcctgagga gaaacccaag acagaggcca agccaagga agatgacaag    2940 accctctcaa aagagcctag caagcctaag gcagaaaagg ctgaaaaatc ctccagcaca    3000
gaccaaaaag acagcaagcc tccagagaag gccacagaag acaaggccgc caagggaag    3060 taa                                                                  3063
```

<210> SEQ ID NO 4
<211> LENGTH: 1020
<212> TYPE: PRT
<213> ORGANISM: Homo sapiens

<400> SEQUENCE: 4

```
Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu Ala His Asn Arg Ser Leu Glu Gly Glu
        115                 120                 125

Ala Ala Ala Leu Arg Gln Gln Gln Ala Gly Arg Ser Ala Met Gly Glu
    130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
        195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335
```

-continued

```
Ser Thr Lys Asp Ser Leu Glu Arg Gln Arg Ser Glu Leu Glu Asp Arg
                340                 345                 350

His Gln Ala Asp Ile Ala Ser Tyr Gln Glu Ala Ile Gln Gln Leu Asp
            355                 360                 365

Ala Glu Leu Arg Asn Thr Lys Trp Glu Met Ala Ala Gln Leu Arg Glu
        370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Glu Cys Arg Ile Gly Phe Gly
                405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Glu Lys Ile Lys Val Val Glu
        435                 440                 445

Lys Ser Glu Lys Glu Thr Val Ile Val Glu Glu Gln Thr Glu Glu Thr
    450                 455                 460

Gln Val Thr Glu Glu Val Thr Glu Glu Glu Lys Glu Ala Lys Glu
465                 470                 475                 480

Glu Glu Gly Lys Glu Glu Gly Gly Glu Glu Glu Ala Glu Gly
                485                 490                 495

Gly Glu Glu Glu Thr Lys Ser Pro Pro Ala Glu Glu Ala Ala Ser Pro
            500                 505                 510

Glu Lys Glu Ala Lys Ser Pro Val Lys Glu Glu Ala Lys Ser Pro Ala
        515                 520                 525

Glu Ala Lys Ser Pro Glu Lys Glu Ala Lys Ser Pro Ala Glu Val
530                 535                 540

Lys Ser Pro Glu Lys Ala Lys Ser Pro Ala Lys Glu Ala Lys Ser
545                 550                 555                 560

Pro Pro Glu Ala Lys Ser Pro Glu Lys Glu Ala Lys Ser Pro Ala
                565                 570                 575

Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
        595                 600                 605

Lys Glu Glu Ala Lys Ser Pro Ala Glu Ala Lys Ser Pro Val Lys Glu
    610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
                645                 650                 655

Lys Glu Glu Ala Lys Ser Pro Glu Lys Ala Lys Ser Pro Val Lys Ala
            660                 665                 670

Glu Ala Lys Ser Pro Glu Lys Ala Lys Ser Pro Val Lys Ala Glu Ala
        675                 680                 685

Lys Ser Pro Glu Lys Ala Lys Ser Pro Val Lys Glu Glu Ala Lys Ser
    690                 695                 700

Pro Glu Lys Ala Lys Ser Pro Val Lys Glu Glu Ala Lys Ser Pro Glu
705                 710                 715                 720

Lys Ala Lys Ser Pro Val Lys Glu Glu Ala Lys Thr Pro Glu Lys Ala
                725                 730                 735

Lys Ser Pro Val Lys Glu Glu Ala Lys Ser Pro Glu Lys Ala Lys Ser
            740                 745                 750

Pro Glu Lys Ala Lys Thr Leu Asp Val Lys Ser Pro Glu Ala Lys Thr
```

```
                755                 760                 765
Pro Ala Lys Glu Glu Ala Arg Ser Pro Ala Asp Lys Phe Pro Glu Lys
        770                 775                 780

Ala Lys Ser Pro Val Lys Glu Glu Val Lys Ser Pro Glu Lys Ala Lys
785                 790                 795                 800

Ser Pro Leu Lys Glu Asp Ala Lys Ala Pro Glu Lys Glu Ile Pro Lys
                805                 810                 815

Lys Glu Glu Val Lys Ser Pro Val Lys Glu Glu Lys Pro Gln Glu
        820                 825                 830

Val Lys Val Lys Glu Pro Pro Lys Ala Glu Glu Lys Ala Pro
            835                 840                 845

Ala Thr Pro Lys Thr Glu Glu Lys Lys Asp Ser Lys Lys Glu Glu Ala
        850                 855                 860

Pro Lys Lys Glu Ala Pro Lys Pro Lys Val Glu Glu Lys Glu Pro
865                 870                 875                 880

Ala Val Glu Lys Pro Lys Glu Ser Lys Val Glu Ala Lys Lys Glu Glu
                885                 890                 895

Ala Glu Asp Lys Lys Lys Val Pro Thr Pro Glu Lys Glu Ala Pro Ala
            900                 905                 910

Lys Val Glu Val Lys Glu Asp Ala Lys Pro Lys Glu Lys Thr Glu Val
        915                 920                 925

Ala Lys Lys Glu Pro Asp Asp Ala Lys Ala Lys Glu Pro Ser Lys Pro
930                 935                 940

Ala Glu Lys Lys Glu Ala Ala Pro Glu Lys Lys Asp Thr Lys Glu Glu
945                 950                 955                 960

Lys Ala Lys Lys Pro Glu Glu Lys Pro Lys Thr Glu Ala Lys Ala Lys
            965                 970                 975

Glu Asp Asp Lys Thr Leu Ser Lys Glu Pro Ser Lys Pro Lys Ala Glu
        980                 985                 990

Lys Ala Glu Lys Ser Ser Ser Thr  Asp Gln Lys Asp Ser  Lys Pro Pro
        995                 1000                1005

Glu Lys Ala Thr Glu Asp Lys  Ala Ala Lys Gly Lys
    1010                1015                1020

<210> SEQ ID NO 5
<211> LENGTH: 2751
<212> TYPE: DNA
<213> ORGANISM: Homo sapiens

<400> SEQUENCE: 5
atgagctaca cgttggactc gctgggcaac ccgtccgcct accggcgggt aaccgagacc       60
cgctcgagct tcagccgcgt cagcggctcc ccgtccagtg gcttccgctc gcagtcgtgg      120
tcccgcggct cgcccagcac cgtgtcctcc tcctataagc gcagcatgct cgccccgcgc      180
ctcgcttaca gctcggccat gctcagctcc gccgagagca gccttgactt cagccagtcc      240
tcgtccctgc tcaacggcgg ctccggaccc ggcggcgact acaagctgtc ccgctccaac      300
gagaaggagc agctgcaggg gctgaacgac cgctttgccg gctacataga aaggtgcac       360 tacctggagc agcagaataa ggagattgag gcggagatcc aggcgctgcg gcagaagcag      420
gcctcgcacg cccagctggg cgacgcgtac gaccaggaga tccgcgagct cgcgccacc       480 ctggagatgg tgaaccacga gaaggctcag gtgcagctgg actcggacca cctggaggaa      540
gacatccacc ggctcaagga gcctttgag gaggaggcgc ggttgcgcga cgacactgag       600
gcggccatcc gcgcgctgcg caaagacatc gaggaggcgt cgctggtcaa ggtggagctg      660
```

-continued

```
gacaagaagg tgcagtcgct gcaggatgag gtggccttcc tgcggagcaa ccacgaggag    720
gaggtggccg accttctggc ccagatccag gcatcgcaca tcacggtgga gcgcaaagac    780
tacctgaaga cagacatctc gacggcgctg aaggaaatcc gctcccagct cgaaagccac    840
tcagaccaga atatgcacca ggccgaagag tggttcaaat gccgctacgc caagctcacc    900
gaggcggccg agcagaacaa ggaggccatc cgctccgcca aggaagagat cgccgagtac    960
cggcgccagc tgcagtccaa gagcatcgag ctagagtcgg tgcgcggcac caaggagtcc   1020
ctggagcggc agctcagcga catcgaggag cgccacaacc acgacctcag cagctaccag   1080
gacaccatcc agcagctgga aaatgagctt cggggcacaa gtgggaaat ggctcgtcat    1140 ttgcgcgaat accaggacct cctcaacgtc aagatggctc tggatataga aatcgctgcg   1200
tacagaaaac tcctggaggg tgaagagact agatttagca catttgcagg aagcatcact   1260
gggccactgt atacacaccg accccccaatc acaatatcca gtaagattca gaaacccaag   1320
gtggaagctc ccaagcttaa ggtccaacac aaatttgtcg aggagatcat agaggaaacc   1380
aaagtggagg atgagaagtc agaaatggaa gaggccctga cagccattac agaggaattg   1440
gccgtttcca tgaaggaaga gaagaaagaa gcagcagaag aaaaggaaga ggaacccgaa   1500
gctgaagaag aagaagtagc tgccaaaaag tctccagtga aagcaactgc acctgaagtt   1560
aaagaagagg aaggggaaaa ggaggaagaa gaaggccagg aagaagagga ggaagaagat   1620
gagggagcta agtcagacca agccgaagag ggaggatccg agaaggaagg ctctagtgaa   1680
aaagaggaag gtgagcagga agaaggaaa acagaagctg aagctgaagg agaggaagcc   1740
gaagctaaag aggaaaagaa agtggaggaa aagagtgagg aagtggctac caaggaggag   1800
ctggtggcag atgccaaggt ggaaaagcca gaaaaagcca agtctcctgt gccaaaatca   1860
ccagtggaag agaaaggcaa gtctcctgtg cccaagtcac cagtggaaga gaaaggcaag   1920
tctcctgtgc ccaagtcacc agtggaagag aaaggcaagt ctcctgtgcc gaaatcacca   1980
gtggaagaga aaggcaagtc tcctgtgtca aaatcaccag tggaagagaa agccaaatct   2040
cctgtgccaa aatcaccagt ggaagaggca agtcaaaag cagaagtggg aaaggtgaa    2100 cagaaagagg aagaagaaaa ggaagtcaag gaagctccca aggaagagaa ggtagagaaa   2160
aaggaagaga accaaagga tgtgccagag aagaagaaag ctgagtcccc tgtaaaggag   2220
gaagctgtgg cagaggtggt caccatcacc aaatcggtaa aggtgcactt ggagaaagag   2280
accaaagaag aggggaagcc actgcagcag gagaaagaga aggagaaagc gggaggagag   2340
ggaggaagtg aggaggaagg gagtgataaa ggtgccaagg gatccaggaa ggaagacata   2400
gctgtcaatg gggaggtaga aggaaaagag gaggtagagc aggagaccaa ggaaaaaggc   2460
agtgggaggg aagaggagaa aggcgttgtc accaatggcc tagacttgag cccagcagat   2520
gaaaagaagg ggggtgataa aagtgaggag aaagtggtgg tgaccaaaac ggtagaaaaa   2580
atcaccagtg aggggggaga tggtgctacc aaatacatca ctaaatctgt aaccgtcact   2640
caaaaggttg aagagcatga agagacccttt gaggagaaac tagtgtctac taaaaaggta   2700
gaaaaagtca cttcacacgc catagtaaag gaagtcaccc agagtgacta a            2751
```

<210> SEQ ID NO 6  
<211> LENGTH: 916  
<212> TYPE: PRT  
<213> ORGANISM: Homo sapiens

<400> SEQUENCE: 6

```
Met Ser Tyr Thr Leu Asp Ser Leu Gly Asn Pro Ser Ala Tyr Arg Arg
1               5                   10                  15

Val Thr Glu Thr Arg Ser Ser Phe Ser Arg Val Ser Gly Ser Pro Ser
            20                  25                  30

Ser Gly Phe Arg Ser Gln Ser Trp Ser Arg Gly Ser Pro Ser Thr Val
        35                  40                  45

Ser Ser Ser Tyr Lys Arg Ser Met Leu Ala Pro Arg Leu Ala Tyr Ser
50                  55                  60

Ser Ala Met Leu Ser Ser Ala Glu Ser Ser Leu Asp Phe Ser Gln Ser
65                  70                  75                  80

Ser Ser Leu Leu Asn Gly Gly Ser Gly Pro Gly Gly Asp Tyr Lys Leu
                85                  90                  95

Ser Arg Ser Asn Glu Lys Glu Gln Leu Gln Gly Leu Asn Asp Arg Phe
                100                 105                 110

Ala Gly Tyr Ile Glu Lys Val His Tyr Leu Glu Gln Gln Asn Lys Glu
            115                 120                 125

Ile Glu Ala Glu Ile Gln Ala Leu Arg Gln Lys Gln Ala Ser His Ala
    130                 135                 140

Gln Leu Gly Asp Ala Tyr Asp Gln Glu Ile Arg Glu Leu Arg Ala Thr
145                 150                 155                 160

Leu Glu Met Val Asn His Glu Lys Ala Gln Val Gln Leu Asp Ser Asp
                165                 170                 175

His Leu Glu Glu Asp Ile His Arg Leu Lys Glu Arg Phe Glu Glu
            180                 185                 190

Ala Arg Leu Arg Asp Asp Thr Glu Ala Ala Ile Arg Ala Leu Arg Lys
        195                 200                 205

Asp Ile Glu Glu Ala Ser Leu Val Lys Val Glu Leu Asp Lys Lys Val
    210                 215                 220

Gln Ser Leu Gln Asp Glu Val Ala Phe Leu Arg Ser Asn His Glu Glu
225                 230                 235                 240

Glu Val Ala Asp Leu Leu Ala Gln Ile Gln Ala Ser His Ile Thr Val
                245                 250                 255

Glu Arg Lys Asp Tyr Leu Lys Thr Asp Ile Ser Thr Ala Leu Lys Glu
            260                 265                 270

Ile Arg Ser Gln Leu Glu Ser His Ser Asp Gln Asn Met His Gln Ala
    275                 280                 285

Glu Glu Trp Phe Lys Cys Arg Tyr Ala Lys Leu Thr Glu Ala Ala Glu
        290                 295                 300

Gln Asn Lys Glu Ala Ile Arg Ser Ala Lys Glu Glu Ile Ala Glu Tyr
305                 310                 315                 320

Arg Arg Gln Leu Gln Ser Lys Ser Ile Glu Leu Glu Ser Val Arg Gly
                325                 330                 335

Thr Lys Glu Ser Leu Glu Arg Gln Leu Ser Asp Ile Glu Glu Arg His
            340                 345                 350

Asn His Asp Leu Ser Ser Tyr Gln Asp Thr Ile Gln Gln Leu Glu Asn
    355                 360                 365

Glu Leu Arg Gly Thr Lys Trp Glu Met Ala Arg His Leu Arg Glu Tyr
370                 375                 380

Gln Asp Leu Leu Asn Val Lys Met Ala Leu Asp Ile Glu Ile Ala Ala
385                 390                 395                 400

Tyr Arg Lys Leu Leu Glu Gly Glu Glu Thr Arg Phe Ser Thr Phe Ala
                405                 410                 415

Gly Ser Ile Thr Gly Pro Leu Tyr Thr His Arg Pro Pro Ile Thr Ile
```

```
                420            425             430
Ser Ser Lys Ile Gln Lys Pro Lys Val Glu Ala Pro Lys Leu Lys Val
            435             440             445
Gln His Lys Phe Val Glu Ile Ile Glu Thr Lys Val Glu Asp
    450             455             460
Glu Lys Ser Glu Met Glu Ala Leu Thr Ala Ile Thr Glu Glu Leu
465             470             475             480
Ala Val Ser Met Lys Glu Glu Lys Glu Ala Glu Glu Lys Glu
                485             490             495
Glu Glu Pro Glu Ala Glu Glu Val Ala Ala Lys Lys Ser Pro
            500             505             510
Val Lys Ala Thr Ala Pro Glu Val Lys Glu Glu Gly Glu Lys Glu
            515             520             525
Glu Glu Glu Gly Gln Glu Glu Glu Glu Asp Glu Gly Ala Lys
            530             535             540
Ser Asp Gln Ala Glu Glu Gly Ser Glu Lys Glu Gly Ser Ser Glu
545             550             555             560
Lys Glu Glu Gly Glu Gln Glu Glu Gly Glu Thr Glu Ala Glu Ala Glu
                565             570             575
Gly Glu Glu Ala Glu Ala Lys Glu Glu Lys Lys Val Glu Glu Lys Ser
                580             585             590
Glu Glu Val Ala Thr Lys Glu Glu Leu Val Ala Asp Ala Lys Val Glu
            595             600             605
Lys Pro Glu Lys Ala Lys Ser Pro Val Pro Lys Ser Pro Val Glu Glu
            610             615             620
Lys Gly Lys Ser Pro Val Pro Lys Ser Pro Val Glu Glu Lys Gly Lys
625             630             635             640
Ser Pro Val Pro Lys Ser Pro Val Glu Glu Lys Gly Lys Ser Pro Val
                645             650             655
Pro Lys Ser Pro Val Glu Glu Lys Gly Lys Ser Pro Val Ser Lys Ser
            660             665             670
Pro Val Glu Glu Lys Ala Lys Ser Pro Val Pro Lys Ser Pro Val Glu
            675             680             685
Glu Ala Lys Ser Lys Ala Glu Val Gly Lys Gly Glu Gln Lys Glu Glu
            690             695             700
Glu Glu Lys Glu Val Lys Glu Ala Pro Lys Glu Glu Lys Val Glu Lys
705             710             715             720
Lys Glu Glu Lys Pro Lys Asp Val Pro Glu Lys Lys Ala Glu Ser
                725             730             735
Pro Val Lys Glu Glu Ala Val Ala Glu Val Val Thr Ile Thr Lys Ser
            740             745             750
Val Lys Val His Leu Glu Lys Glu Thr Lys Glu Glu Gly Lys Pro Leu
            755             760             765
Gln Gln Glu Lys Glu Lys Glu Lys Ala Gly Gly Glu Gly Gly Ser Glu
            770             775             780
Glu Glu Gly Ser Asp Lys Gly Ala Lys Gly Ser Arg Lys Glu Asp Ile
785             790             795             800
Ala Val Asn Gly Glu Val Glu Gly Lys Glu Glu Val Glu Gln Glu Thr
                805             810             815
Lys Glu Lys Gly Ser Gly Arg Glu Glu Glu Lys Gly Val Val Thr Asn
            820             825             830
Gly Leu Asp Leu Ser Pro Ala Asp Glu Lys Lys Gly Gly Asp Lys Ser
            835             840             845
```

```
Glu Glu Lys Val Val Val Thr Lys Thr Val Glu Lys Ile Thr Ser Glu
    850                 855                 860

Gly Gly Asp Gly Ala Thr Lys Tyr Ile Thr Lys Ser Val Thr Val Thr
865                 870                 875                 880

Gln Lys Val Glu Glu His Glu Glu Thr Phe Glu Glu Lys Leu Val Ser
                885                 890                 895

Thr Lys Lys Val Glu Lys Val Thr Ser His Ala Ile Val Lys Glu Val
            900                 905                 910

Thr Gln Ser Asp
        915

<210> SEQ ID NO 7
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 7
atgagttcct tcagctacga gc                                          22

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
ctgggcatca acgatccaga                                             20
```